(12) United States Patent
Baker et al.

(10) Patent No.: US 11,116,792 B1
(45) Date of Patent: Sep. 14, 2021

(54) CERIUM OXIDE NANOPARTICLE FORMULATION FOR USE IN SKIN RADIOPROTECTION AND ASSOCIATED METHODS

(71) Applicant: BioCurity Holdings, Inc., Jupiter, FL (US)

(72) Inventors: Cheryl H. Baker, New Smyrna Beach, FL (US); D. Wayne Jenkins, Winter Park, FL (US); Sudipta Seal, Orlando, FL (US)

(*) Notice: Subject to any disclaimer, the term of this patent is extended or adjusted under 35 U.S.C. 154(b) by 0 days.

(21) Appl. No.: 14/860,044

(22) Filed: Sep. 21, 2015

Related U.S. Application Data

(63) Continuation of application No. 14/317,895, filed on Jun. 27, 2014, now abandoned, which is a continuation of application No. 13/334,911, filed on Dec. 22, 2011, now abandoned.

(60) Provisional application No. 61/425,904, filed on Dec. 22, 2010.

(51) Int. Cl.
*A61K 9/107* (2006.01)
*A61K 33/24* (2019.01)

(52) U.S. Cl.
CPC .................... *A61K 33/24* (2013.01)

(58) Field of Classification Search
CPC ........ A61K 9/1075; A61K 9/107; A61K 9/14; A61K 9/16; A61K 9/1605
USPC ................................................ 424/464–489
See application file for complete search history.

(56) References Cited

U.S. PATENT DOCUMENTS

| | | | |
|---|---|---|---|
| 6,060,041 A * | 5/2000 | Candau ............ | A61Q 17/04 424/59 |
| 6,955,639 B2 | 10/2005 | Hainfeld et al. | |
| 7,347,987 B2 | 3/2008 | McGinnis et al. | |
| 7,504,356 B1 | 3/2009 | Self et al. | |
| 7,534,453 B1 | 5/2009 | Rzigalinski et al. | |
| 7,727,559 B2 | 6/2010 | McGinnis et al. | |
| 8,048,523 B2 | 11/2011 | Kambe et al. | |
| 2003/0231992 A1 | 12/2003 | Sarkas et al. | |
| 2006/0194057 A1* | 8/2006 | Pfluecker ........ | A61K 8/046 428/404 |
| 2006/0246152 A1 | 11/2006 | McGinnis et al. | |
| 2008/0003183 A1 | 1/2008 | Guo | |
| 2009/0092671 A1 | 4/2009 | Rzigalinski et al. | |
| 2009/0111040 A1* | 4/2009 | Veregin .......... | G03G 9/09716 430/108.3 |
| 2009/0297626 A1* | 12/2009 | O'Brien .......... | A61K 33/24 424/642 |
| 2010/0166821 A1 | 7/2010 | Rzigalinski et al. | |

FOREIGN PATENT DOCUMENTS

| | | | | |
|---|---|---|---|---|
| EP | 2103553 A1 * | 9/2009 | ............ | B65D 85/68 |
| WO | WO 2007/002662 A2 | 1/2007 | | |
| WO | WO 2007002662 A2 * | 1/2007 | ............ | A61K 9/14 |
| WO | WO-2007002662 A2 * | 1/2007 | ............ | A61P 17/02 |

OTHER PUBLICATIONS

Tarnuzzer et al (Vacancy Engineered Ceria Nanostructures for Protection from Radiation-Induced Cellular Damage, Nano Letters, vol. 5, No. 12, 2005) (Year: 2005).*

Colon et al (Protection from radiation-induced pneumonitis using cerium oxide nanoparticles; Nanomedicine: Nanotechnology, Biology, and Medicine, May 2009, 225-231) (Year: 2009).*

Stone et al (Effects of radiation on normal tissue: consequences and mechanisms; The Lancet, Oncology, vol. 4, Sep. 2003) (Year: 2003).*

Niu, Jianli et al, Cardioprotective Effects of Cerium Oxide Nanoparticles in a Transgenic Murine Model of Cardiomyopathy; Cardiovasc Res., Feb. 1, 2007: 73(3); 549-559. Epub8b, Nov. 30, 2006.

Tarnuzzer, Roy W. el al; Vacancy Engineered Ceria Nanostructures for Protection from Radiation-Induced Cellular Damage; Nano Lett, Dec. 5, 2005 (12); 2573-2577.

J Lin, W. et al; Toxicity of Cerium Oxide Nanoparticles in Human Lung Cancer Cells; Intl. J. Toxicol, Nov.-Dec. 25, 2006(6); 451-7.

Naito, Y. el al; Oxidative Stress-Related Molecules as a Therapeutic Target for Inflammatory and Allergic Diseases; Cur Drug Targets Inflamm Allergy; (Aug. 2005; (4}; 511-515.

Hu, Kenneth et al.; Rationale for Integrating High-Dose Rate Intraoperative Radiation (HDR-IORT) and Postoperative External Beam Radiation With Subcutaneous Amifostine for the Management of Stage III/IV Head and Neck Cancer; Semin Oncol, Dec. 30, 2003; (6 Suppl 18); 40-48.

Korsvik, C. et al; Superoxide Dismutase Mimetic Properties Exhibited by Vacancy Engineering Ceria Nanoparticles; ChemComm. Jan. 4, 2007.

Colon et al. (Protection from radiation-induced pheumonitis using cerium oxide naoparticles; Nanomedicine; Nanotechnology, Biology, and Medicine, May 2009, 225-231) (Year 2009).

* cited by examiner

*Primary Examiner* — Micah Paul Young
(74) *Attorney, Agent, or Firm* — Taft Stettinius & Hollister LLP; Joseph M. Bennett-Paris

(57) ABSTRACT

Cerium oxide nanoparticles have been found to enhance radiation-induced cancer cell death, while at the same time protecting normal tissue from radiation. The combination of cerium oxide nanoparticles with radiation has also been found to control and/or minimize the metastatic index. Cerium oxide nanoparticles have also been found to protect normal tissue subjected to irradiation from inflammation, and further to protect cells from reactive oxygen species. A cream comprising cerium oxide nanoparticles is formulated and used to protect skin against radiation-induced dermatitis.

18 Claims, 28 Drawing Sheets

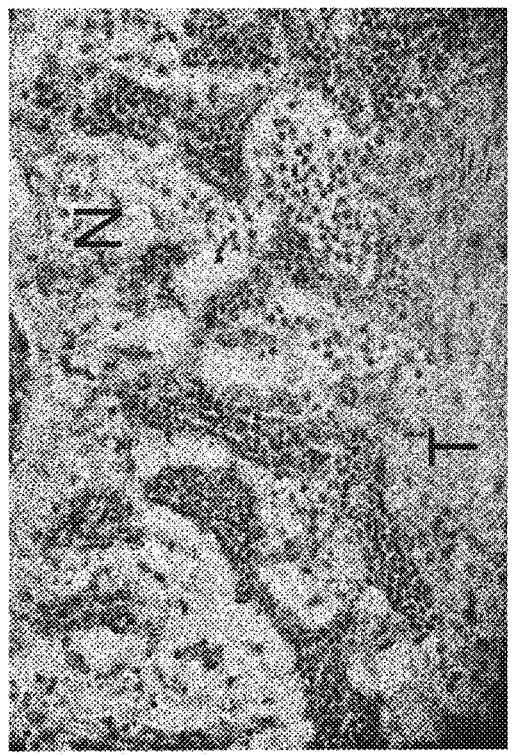
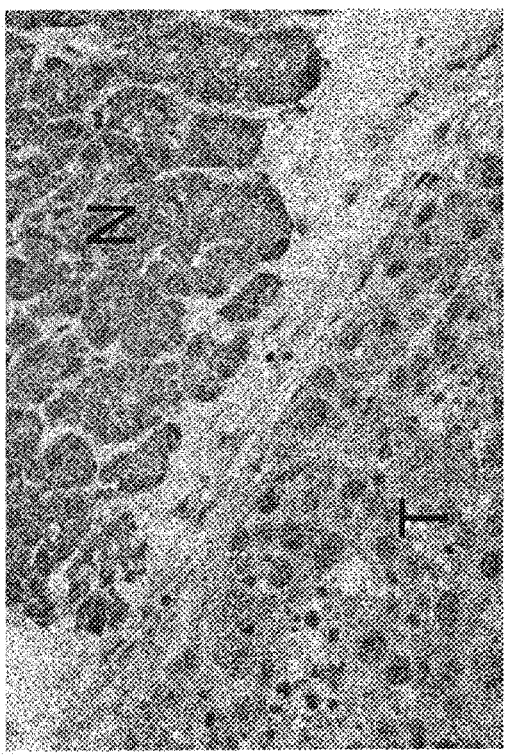
FIG. 10A
A
(Radiation alone)
FIG. 10B
B
(Radiation + CeO₂)
T = Tumor
N = Normal

CeO2 effect on L3.6pl cells in vitro 24 hrs after 12 Gy IR

CeO2 effect on L3.6pl cells in vitro 48 Hrs after 12 Gy IR

FIG. 23A  FIG. 23B  FIG. 23C  FIG. 23D
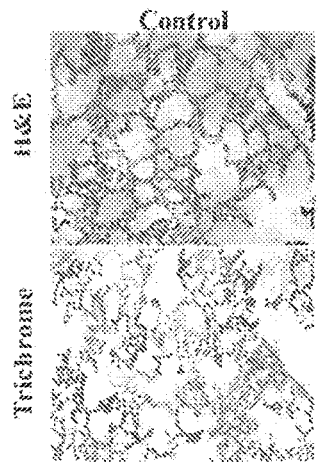
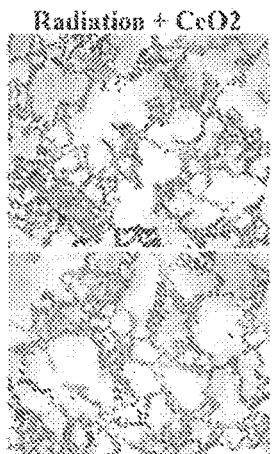
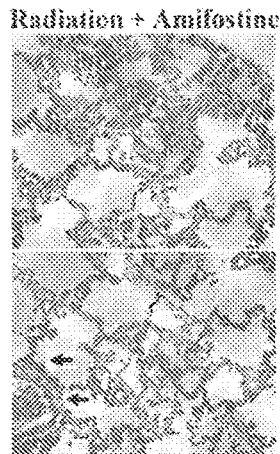
FIG. 23E  FIG. 23F  FIG. 23G  FIG. 23H
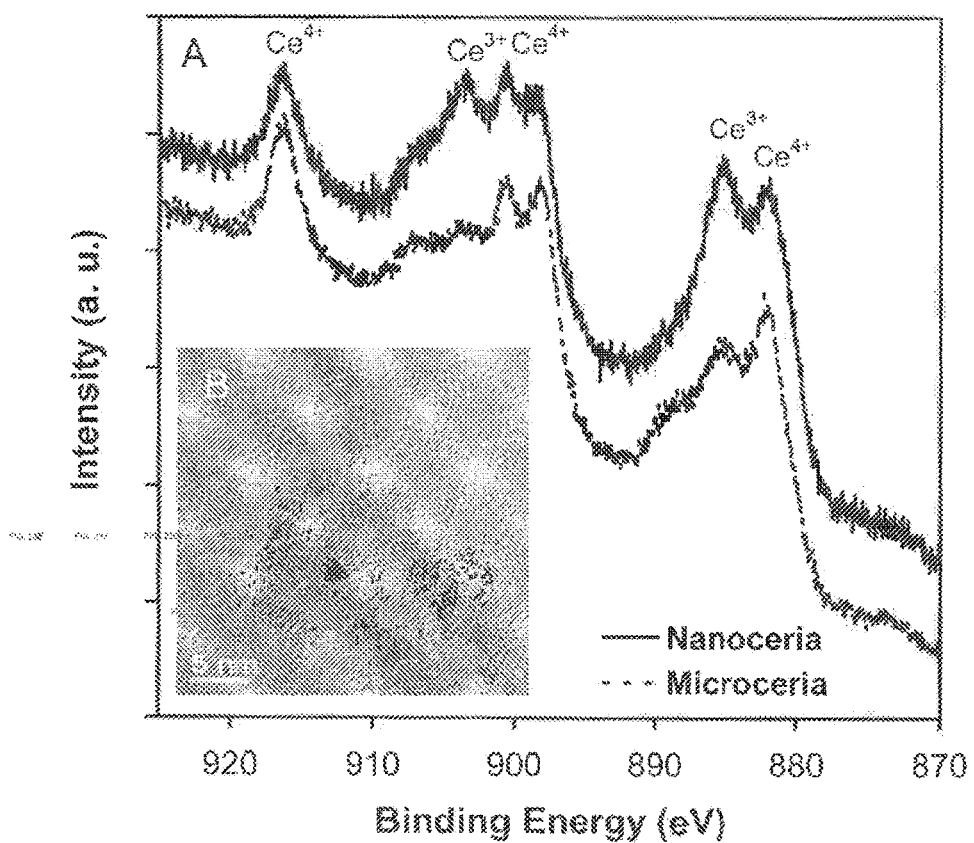
FIG. 24

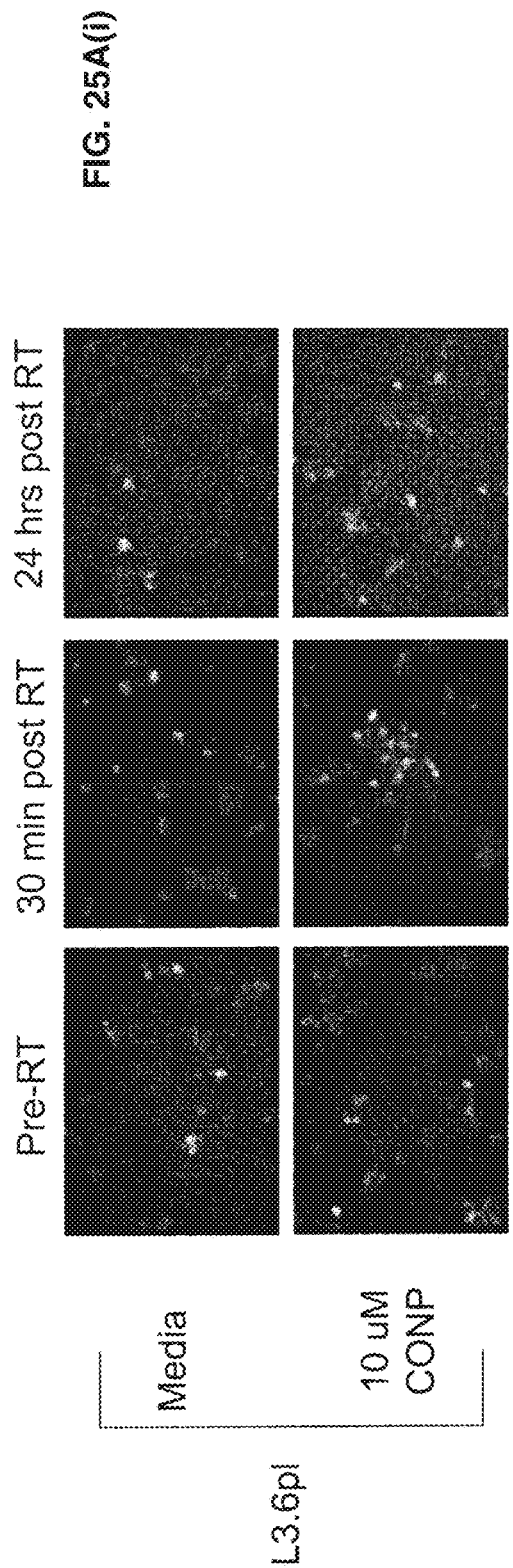
FIG. 25A(i)
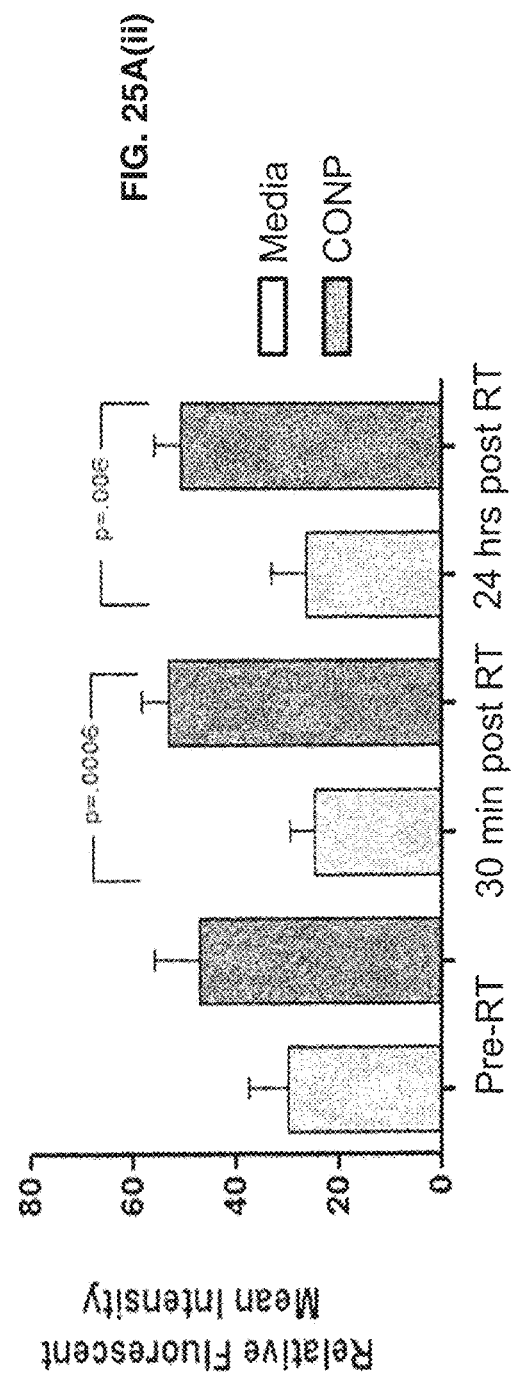
FIG. 25A(ii)

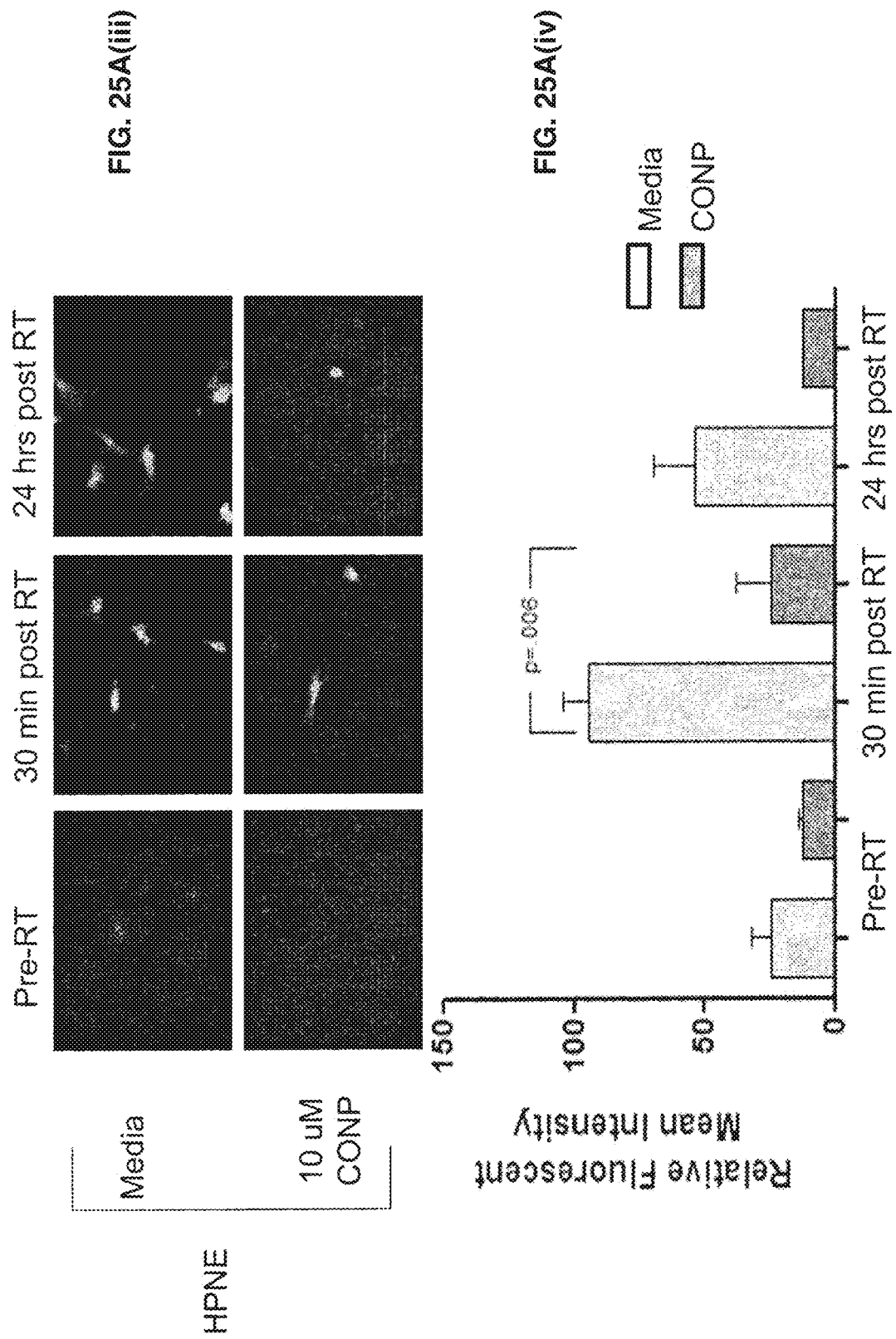

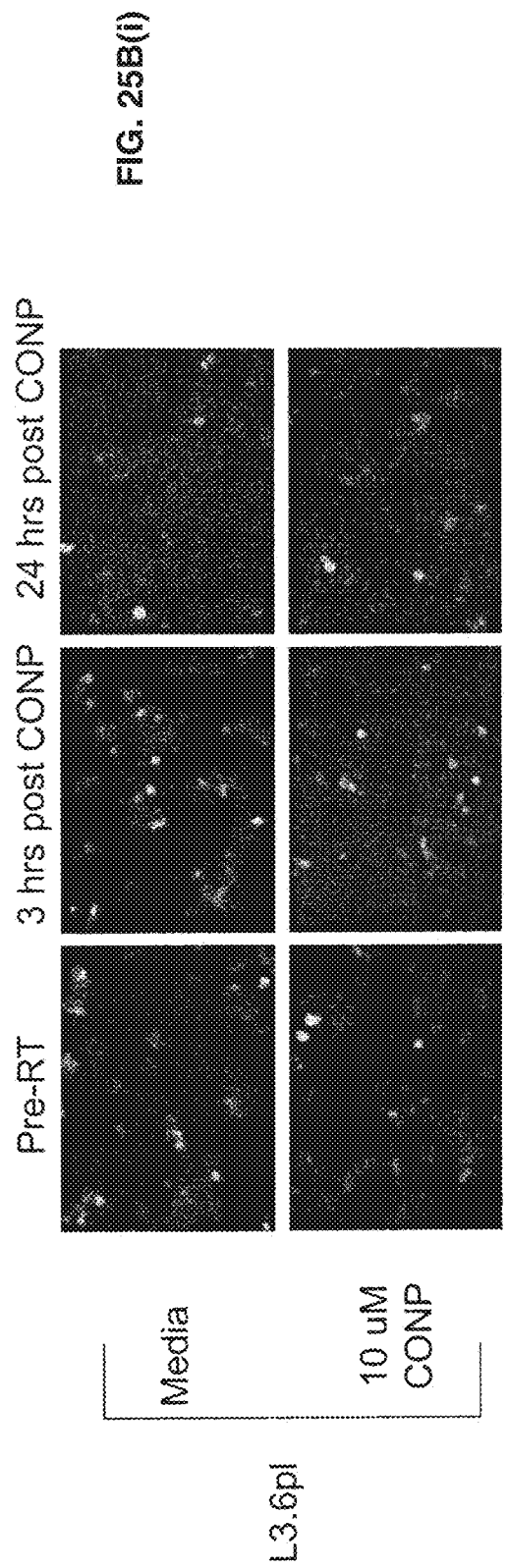
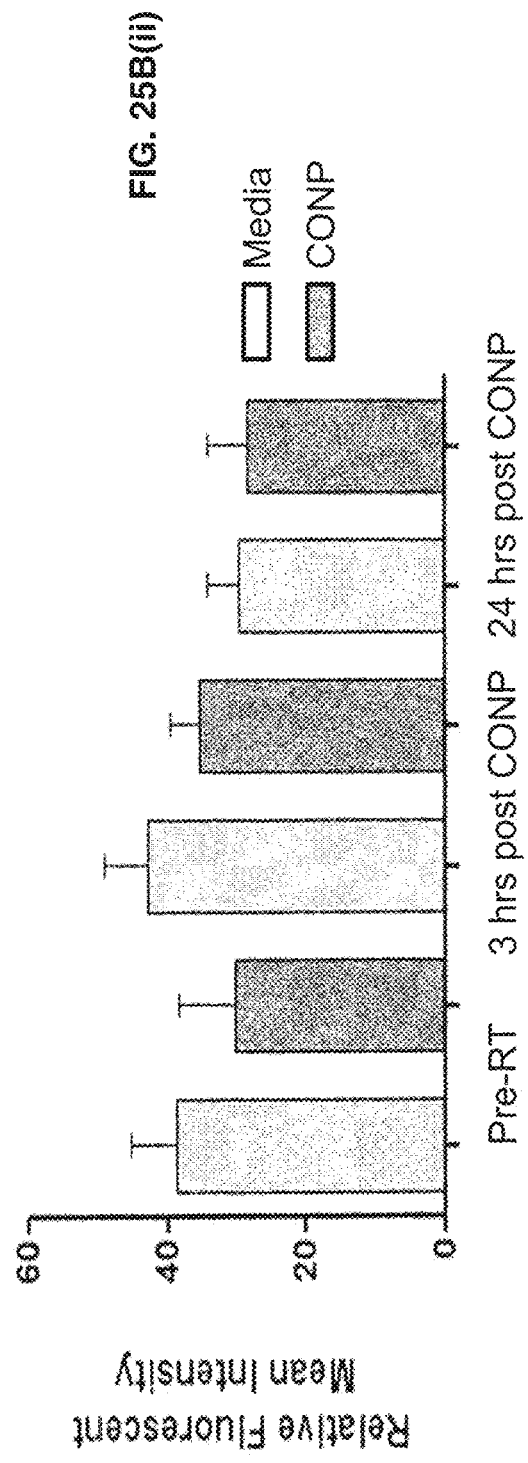
FIG. 25B(i)
FIG. 25B(ii)

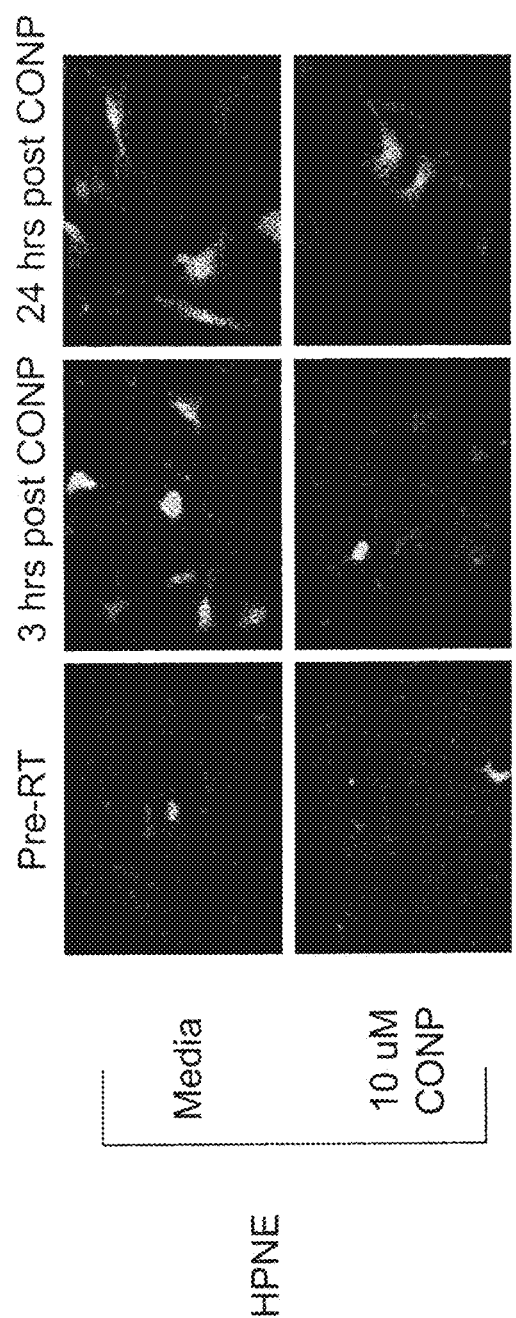
FIG. 25B(iii)
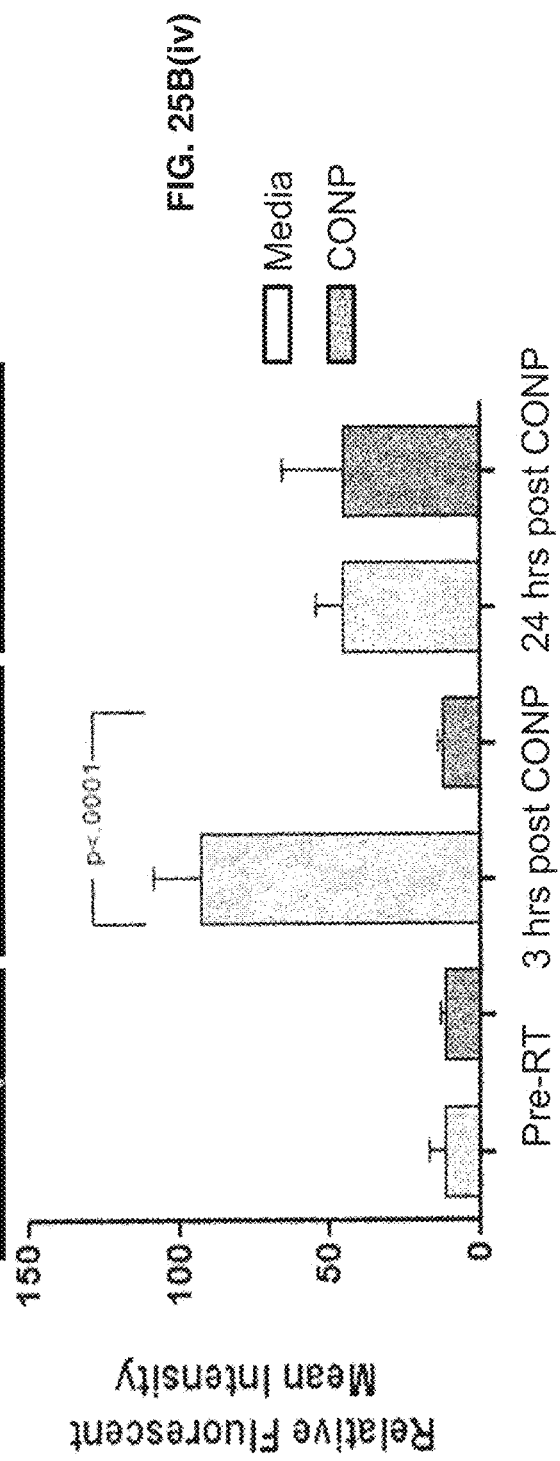
FIG. 25B(iv)

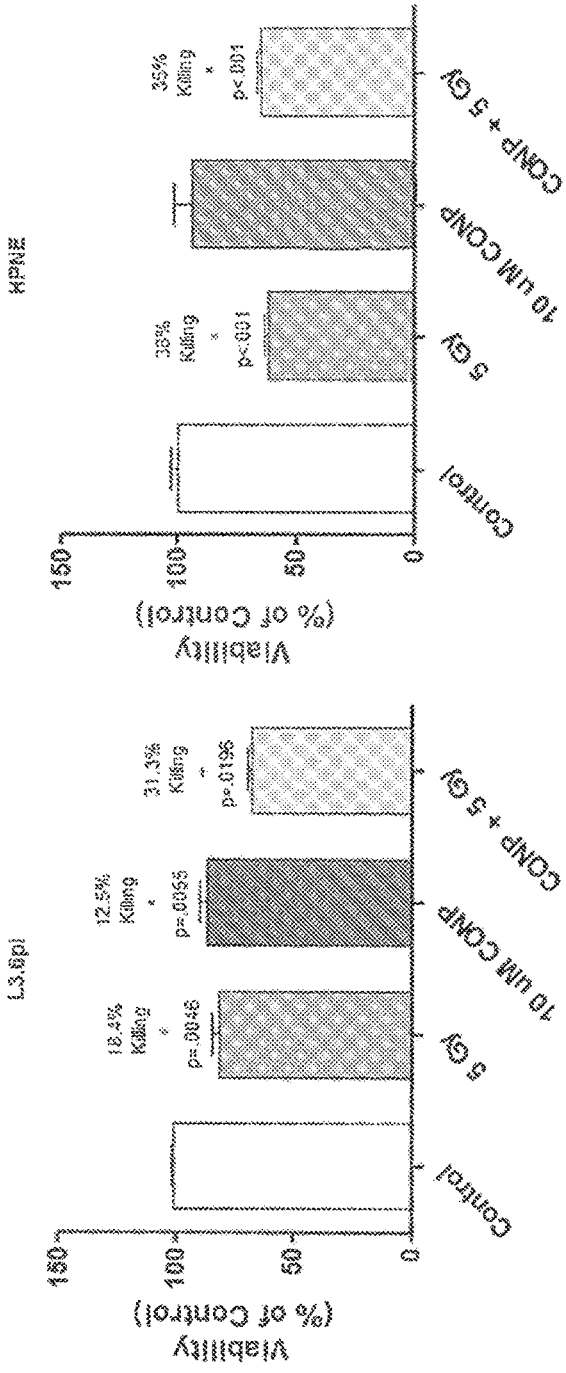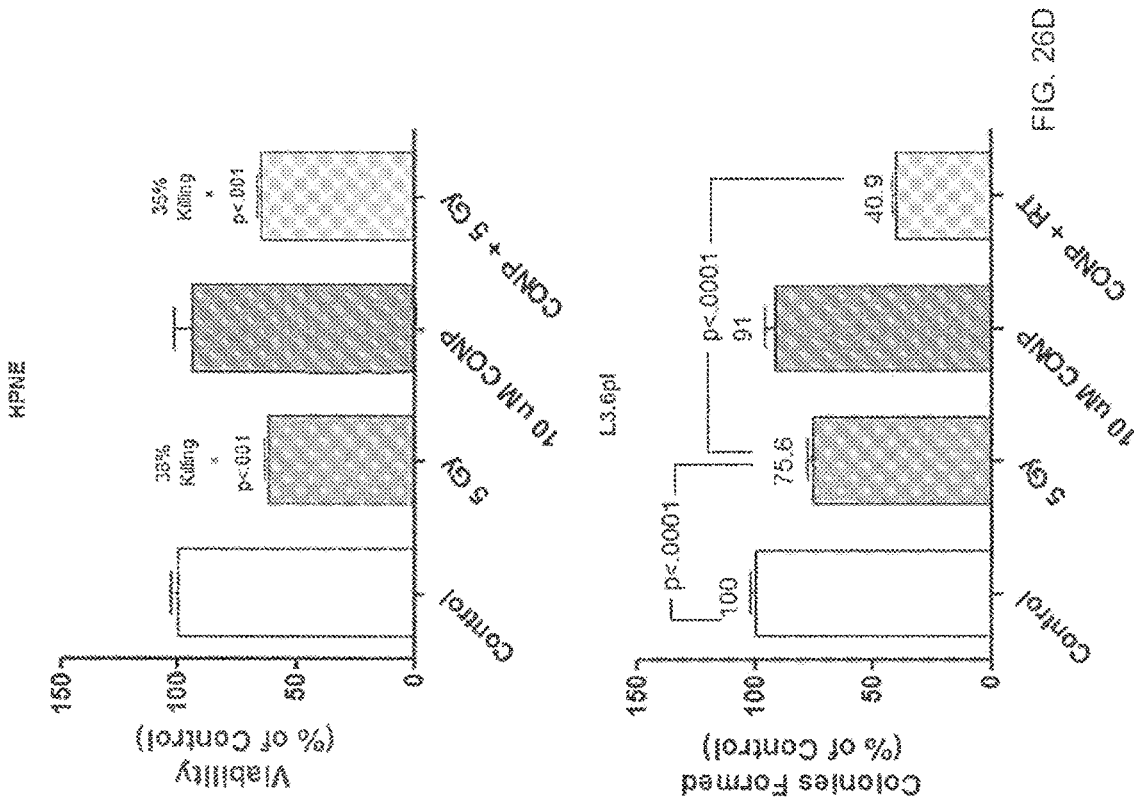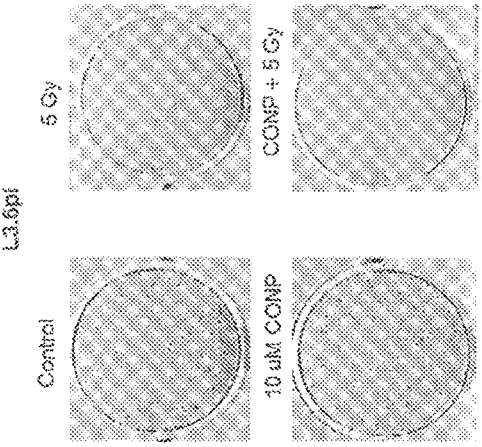

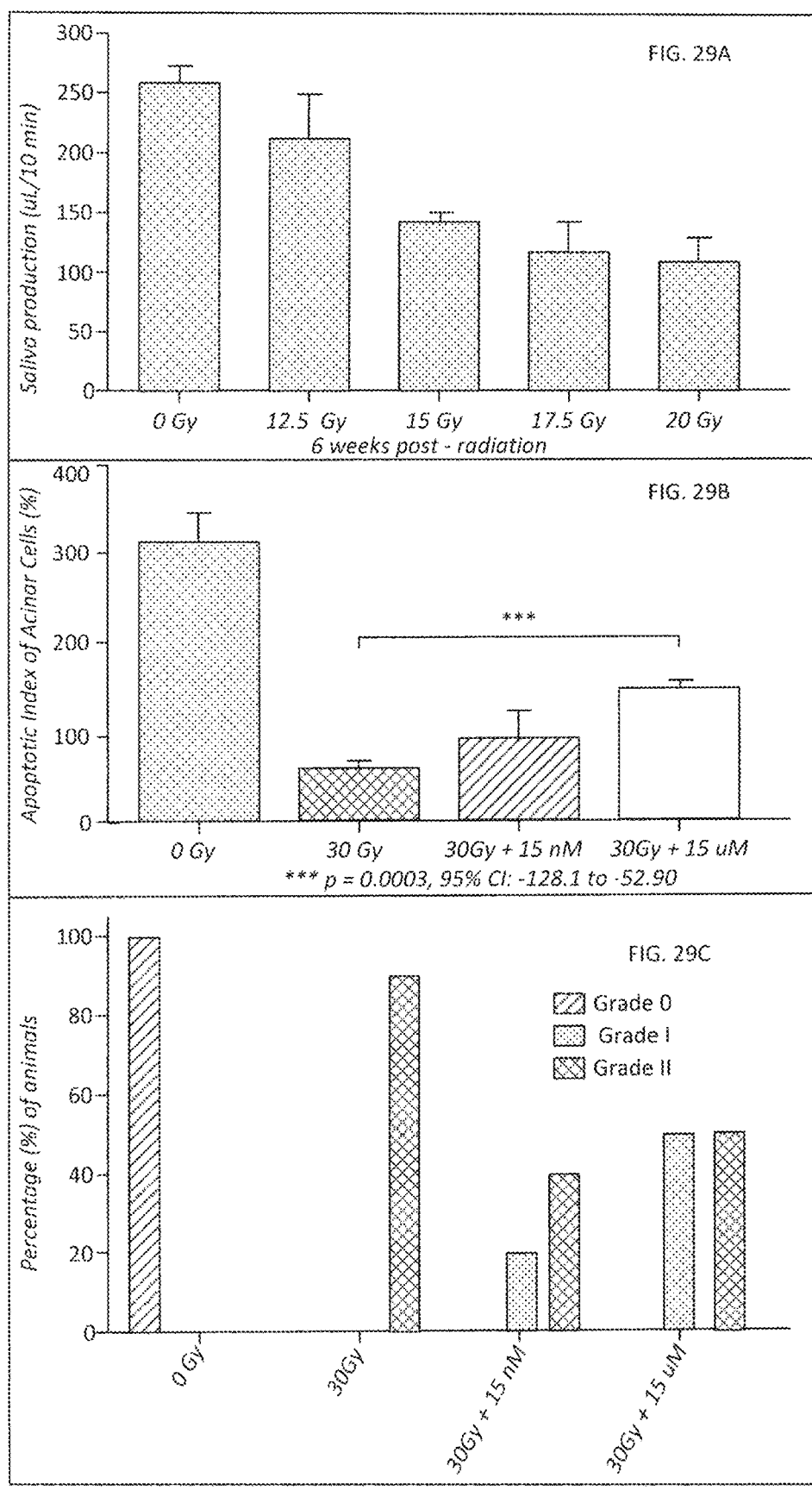

CERIUM OXIDE NANOPARTICLE FORMULATION FOR USE IN SKIN RADIOPROTECTION AND ASSOCIATED METHODS

CROSS REFERENCE TO RELATED APPLICATION

This application is a continuation of U.S. patent application Ser. No. 14/317,895, filed Jun. 27, 2014 for Cerium Oxide Nanoparticle Formulation for Use in Skin Radioprotection And Associated Methods, which is a continuation of U.S. patent application Ser. No. 13/334,911, filed Dec. 22, 2011, for Cerium Oxide Nanoparticle Formulation for Use in Skin Radioprotection And Associated Methods, which claims the benefit of U.S. Provisional Application No. 61/425,904 filed Dec. 22, 2010 for Cerium Oxide Nanoparticle Formulation for Use in Skin Radioprotection and Associated Methods, the disclosure of which are hereby incorporated by reference herein in their entirety, and commonly owned.

FIELD OF INVENTION

The present invention generally relates to compositions and methods for radioprotection during radiation treatment, and more particularly to such compositions and methods utilizing nanoparticle technology, and most particularly to such nanoparticle compositions comprising a cerium oxide-based cream.

BACKGROUND

While radiation can be an effective therapy for cancer, its deleterious effects include damage to normal cells surrounding the target tumor, including the skin. Irradiation causes the formation of free radicals by ionizing reactions, and the free radicals then react with DNA and RNA, causing tissue death. Uncontrolled radical production is also tied to multiple pathological diseases, with radiation damage to macromolecules linearly associated with radiation dose.

For example, dermatitis, also known as inflammation of the skin, is one of the major complaints of patients receiving radiation therapy. It is considered a significant and unpleasant side effect that needs to be reduced. The degree of skin damage is directly correlated to the doses and frequency of radiation treatment, since the delivered radiation causes damage of the skin in the radiation path. To date, several compounds have been developed to prevent these side effects. However, only one, called Amifostine, is currently in clinical use. There are several barriers to its widespread application, and it has not been validated for the protection of skin from the effects of radiation. Therefore, alternative solutions are needed.

Nanoparticles (NP) are sub-micron-sized polymeric colloidal particles that can have a therapeutic agent encapsulated within their polymeric matrix, or adsorbed or conjugated onto the surface. Polymeric nanoparticles constitute a versatile drug delivery system that can potentially overcome physiological barriers and guide drugs to specific cells or intracellular compartments, either by passive or ligand-mediated targeting approaches.

These compositions also allow control of the release pattern of the drug and the sustaining of drug levels for a long time by appropriately selecting the polymeric carriers. The versatility of formulation, colloidal size, biocompatibility, and sustained release properties of nanoparticles have enabled their use in a wide range of applications. A recent strategy comprises the use of "functionalized nanoparticles," wherein the surface characteristics of nanoparticles are tailored to achieve specific ligand-mediated targeting of therapeutic and imaging agents.

Radiation therapy has been a major modality employed in the treatment of head and neck cancer for decades. Unfortunately, the tissues in the head and neck region are exquisitely sensitive to the acute and late effects of radiation treatment. Due to these toxicities, head and neck cancer patients have a uniquely difficult time during a course of radiation. Many patients will require hospitalization, feeding tube placement, pain medications, and intravenous hydration in order to complete the prescribed course of treatment. Moreover, these patients often face long-term difficulties with eating, speaking, tasting, dry mouth, decreased range of motion, and wound healing. The need to improve toxicity associated with the radiotherapeutic treatment of head and neck cancer is significant.

The field of radiation oncology has worked diligently over the last decade to improve radiation delivery techniques in order to spare sensitive structures from the effects of ionizing radiation. These techniques have resulted in improved functional outcomes compared to prior, more rudimentary, radiation techniques. However, the need to attain adequate tumor coverage and the exquisite radiosensitivity of certain normal structures in the head and neck are intrinsic limitations to the magnitude of function and quality of life that can be preserved with these techniques. Hence, even with the implementation of these techniques many patients still experience significant acute and late toxicity after radiation treatment that adversely impacts their quality of life.

To further improve toxicity outcomes in this patient population, we must continue to develop strategies to protect normal tissues from radiation-induced damage. One such strategy is the development of radiation protectors. Several compounds have been described, but amifostine remains the only agent currently in clinical use. Major limitations to the clinical use of amifostine are its short half-life, daily dosing requirements, toxicity based on route of administration, and its cost. Recently published American Society of Clinical Oncology (ASCO) guidelines state that amifostine "may be considered during fractionated radiation therapy. However, these guidelines do not support the use of amifostine in the use of concurrent chemoradiation, which is presently the standard of care in the treatment of many head and neck cancer patients. Moreover, the ability of amifostine to ameliorate radiation induced dermatitis and mucositis has not been adequately established. Hence, there remains a substantial clinical need for a radioprotective agent that can be delivered with relative ease, is long lasting, well-tolerated, and can protect a spectrum of sensitive normal tissues that are responsible for a significant reduction in quality of life.

It would be beneficial to create a composition that could incorporate into nanoparticles a compound that could shield normal tissue, particularly skin, from radiation damage and prevent the onset of radiation-induced dermatitis.

SUMMARY

The present invention is directed to the use of cerium oxide ($CeO_2$) nanoparticles, which can scavenge free radicals in radioprotection, to protect skin from radiation-induced dermatitis. Cerium is a rare earth element of the lanthanide series, having a fluorite lattice structure. The cerium atom can exist in either a 3+ or 4+ state and may transform back and forth in a redox reaction. It is known that cerium oxides make excellent oxygen buffers. The defect structure of nano-$CeO_2$ is dynamic and may change spontaneously or in response to physical conditions such as temperature, pH, and oxygen partial pressure.

Cerium oxide nanoparticles have been found to enhance radiation-induced cancer cell death, while at the same time protecting normal tissue from radiation. Cerium oxide nanoparticles have been found to protect normal tissue subjected to irradiation from inflammation, and further to protect cells from reactive oxygen species (ROS).

Extremely small, microscopic particles, known as nanoparticles, of cerium oxide can provide an effective role in diminishing the skin damage typically seen in patients receiving radiation therapy.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention.

The teachings of the present invention address a novel approach for the protection of normal tissues against radiation-induced damage by using cerium oxide ($CeO_2$) nanoparticles. $CeO_2$ nanoparticles have been tested for their ability to serve as free radical scavengers to render protection against chemical, biological, and radiological insults that promote the production of free radicals. It was suggested that the unique structure of $CeO_2$ nanoparticles, with respect to valence and oxygen defects, promotes cell longevity and decreases toxic insults by virtue of its antioxidant properties, prevents the accumulation of reactive oxygen species (ROS), and thereby prevents the activation of the apoptotic response and cell death.

Previous work has tested the safety and ability of $CeO_2$ nanoparticles to confer radioprotection in a murine model. $CeO_2$ nanoparticles are well tolerated and appear to decrease the incidence of pneumonitis in athymic nude mice. In the instant disclosure, it is hypothesized that $CeO_2$ nanoparticles represent a novel approach to the protection of salivary and skin tissue from radiation-induced damage and test their efficacy as a new radioprotective compound on athymic nude mice receiving radiotherapy to the head and neck.

Advantages offered by the present invention will become more fully apparent as the description that now follows is read in conjunction with the accompanying drawing.

BRIEF DESCRIPTION OF THE DRAWINGS

Embodiments of the invention are described by way of example with reference to the accompanying drawings in which:

FIGS. 10A,10B are histological slides of pancreatic tumor tissue with radiation alone (FIG. 10A) and radiation plus cerium oxide (FIG. 10B);

FIGS. 23A-23H illustrate tissue sections under varying conditions with and without radiation, cerium oxide nanoparticles, and Amifostine;

FIG. 24 plots x-ray photoelectron spectra for $Ce^{3+}$ and $Ce^{4+}$ in nanoceria and microceria, with the inset a high-resolution transmission electron microscopy image of nanoceria particle;

FIGS. 25A(i-iv),25B(i-iv) illustrate cerium oxide nanoparticles (CONPs) selectively increase RT induced ROS in pancreatic cancer cells, wherein FIG. 25A illustrate L3.6p1 cells and FIG. 25A(iii, iv) illustrate hTERT-HPNE cells pre-incubated with CONPs, FIG. 25B illustrate CONPs added after radiation in L3.6p1 cells (i, ii) and FIG. 25B(iii, iv) illustrate CONPs added after radiation in hTERT-HPNE cells;

FIGS. 26A-26D illustrate CONPs selectively sensitize pancreatic cancer cells to radiation in vitro, wherein FIG. 26A illustrates pre-treatment of L3.6p1 cells with 10 μM (0.067 mg/kg) CONPs, FIG. 26B pre-treatment of normal pancreatic cells (HPNE) with 10 μM (0.067 mg/kg) CONPs, FIG. 26C pre-treatment of L3.6p1 cells with 10 μM (0.067 mg/kg) CONPs, and FIG. 26D illustrates the changes in colony formation;

FIG. 28A-28C illustrate physiochemical properties of the synthesized nanoparticles, wherein FIG. 28A illustrates HRTEM image of nanoceria showing nanoparticles size range of 3-5 nm, in the inset high magnification image of the nanoparticle, FIG. 28B illustrates a SEAD pattern of a the fluorite crystal structure where A, B, C and D corresponds to different lattice pattern 111, 200, 220 and 311, respectively, and FIG. 28C illustrates the hydrodynamic radius of the nanoparticle in the size range ~10 nm;

FIG. 29A-29C illustrate radiation effects on salivary production in the absence and presence of cerium oxide nanoparticles, wherein FIG. 29A illustrates stimulated sialometry analysis of salivary gland function 6 weeks after single fraction radiation to the head and neck area (12.5 Gy, 15 Gy, 17.5 Gy or 20 Gy), FIG. 29B the effects of nanoceria on salivary flow protection after radiation exposure, and FIG. 29C the effects of nanoceria on skin hyperpigmentation after radiation exposure using the NCI common terminology criteria for adverse events (CTCAE v.3.0);

FIGS. 31A,31B illustrate effects of cerium oxide nanoparticles on the apoptotic index of salivary glands parenchymal cells after radiation to the head and neck region, wherein FIG. 31A illustrates radiation induced apoptosis of salivary glands parenchymal cells, and FIG. 31B complementary analysis of the effects of $CeO_2$ nanoparticles combined with radiation on all major salivary gland yielded a similar response as that shown in FIG. 31A.

DETAILED DESCRIPTION OF THE PREFERRED EMBODIMENTS

The present invention will now be described more fully hereinafter with reference to the accompanying drawings, in which embodiments of the invention are shown by way of illustration and example. This invention may, however, be embodied in many forms and should not be construed as limited to the embodiments set forth herein. Rather, these embodiments are provided so that this disclosure will be thorough and complete, and will fully convey the scope of the invention to those skilled in the art.

Cerium oxide nanoparticles, preferably non-agglomerated 3-5-nm particles, can be prepared by the microemulsion process, as known in the art. It has been reported that cerium oxide nanoparticles can increase neuronal and brain cell lifespan in culture, and also reduce hydrogen peroxide- and ultraviolet light-induced cell injury. Since free radical scavengers can act as radioprotectants, it was desired to determine whether cerium oxide nanoparticles could confer radioresistance to normal cells, while not affecting cell death in tumor cells.

Figure 1:
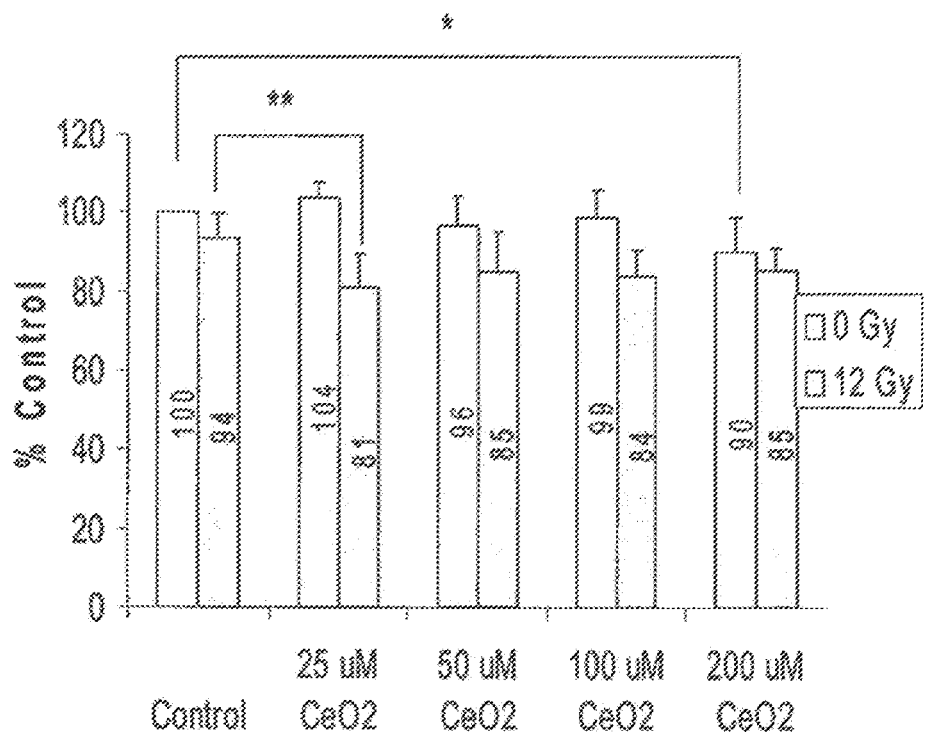
FIGS. 1,2 are graphs of the results of 24 h (FIG. 1) and 48 h (FIG. 2) MTT assays to determine the effect of cerium oxide nanoparticles on L3.6p1 human pancreatic cancer cells.
Figure 2:
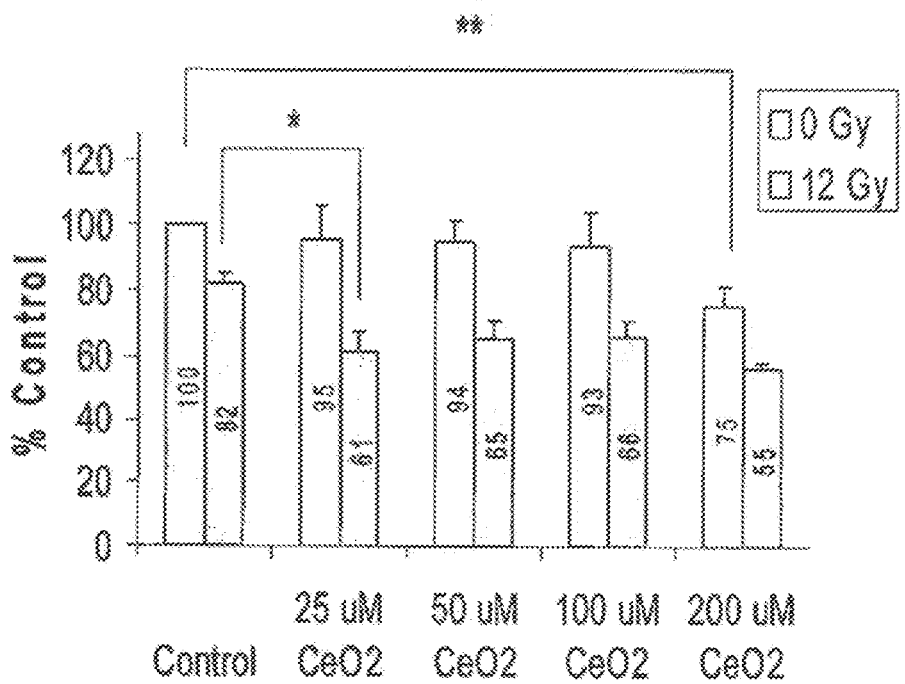

FIGS. 1 and 2 illustrate the results of the presence of cerium oxide nanoparticles on L3.6p1 human pancreatic cancer cells. The white bars represent unirradiated cells; the grey bars represent cells irradiated at 12 Gy. An MTT assay was performed after 24 h (FIG. 1) and 48 h (FIG. 2) to determine the radioprotection and/or cytotoxicity of cerium oxide. It was determined from these data that all cerium oxide concentrations, from 25 to 200 µM, enhanced the radiation-induced death of these cells. The cytotoxicity of 200 µM $CeO_2$ was more significant at 48 h (FIG. 2) than at 24 h (FIG. 1).

Figure 3:
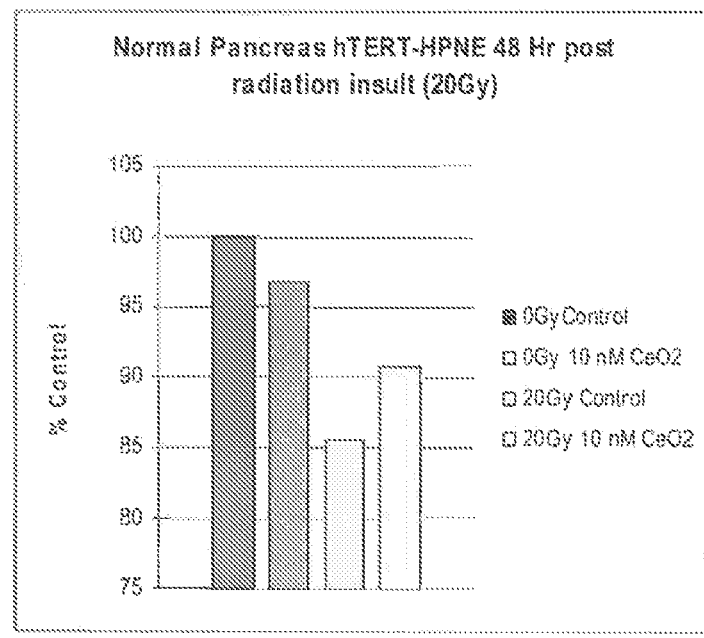
FIGS. 3,4 are graphs of normal hTERT HPNE (FIG. 3) and pancreatic L3.6p1 cell lines 48 h post radiation insult.
Figure 4:
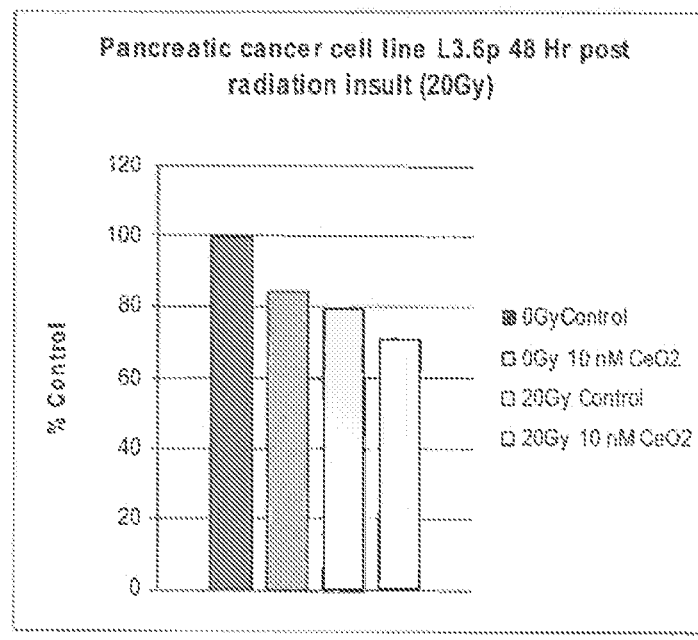

A study of radiation-induced cell death in normal pancreatic hTERT HPNE cell line (FIG. 3) and the L3.6p1 pancreatic cancer cell line (FIG. 4) was performed by plating cells in white-walled 96-well plates (20,000/well) and left attached overnight. After 24 h, some cells were treated with the saline vehicle, and some, with a nanoparticle solution containing 10 nM $CeO_2$, and returned to incubation at 5% $CO_2$ 37° C., for 24 h. After incubation, some of the plates were irradiated with a single dose of 20 Gy, and the plates were returned to the incubator. After 48 h, cell proliferation was assessed with the use of an ATP luminescence assay. Increased cell death is observed in the 20 Gy control for the normal cells, with radioprotection indicated in the presence of cerium oxide nanoparticles.

Figure 5:
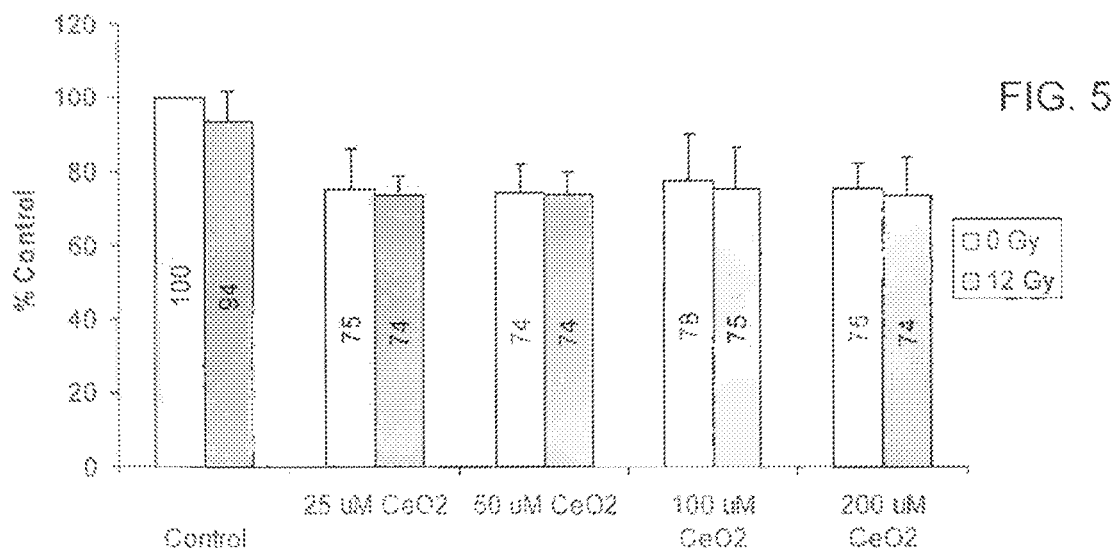
FIGS. 5,6 are graphs of the results of 24 h (FIG. 5) and 48 h (FIG. 6) MIT assay to determine the effect of cerium oxide on Panc-1 human pancreatic cancer cells.
Figure 6:
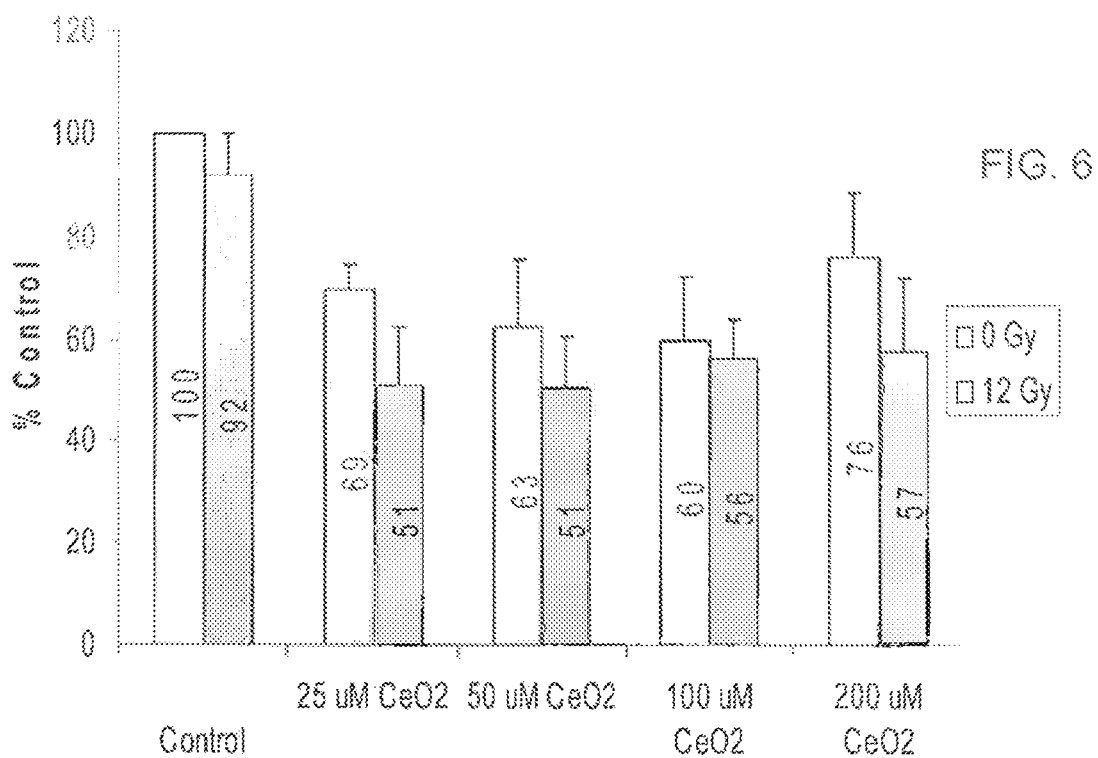

FIGS. 5 and 6 illustrate the radioprotective and/or cytotoxicity effects of $CeO_2$ nanoparticles on Panc-1 human pancreatic cancer cells. The assays performed were MTT assays at 24 h (FIG. 5) and 48 h (FIG. 6). It was found that $CeO_2$ nanoparticles at all concentrations were cytotoxic to Panc-1 cells, in both the presence and the absence of radiation. There was no commensurate significant enhancement of radiation-induced death at 24 h, but there was enhanced radiation-induced death at 48 h. Therefore, $CeO_2$ nanoparticles on human pancreatic cancer cells did not protect against radiation-induced death.

Figure 7:
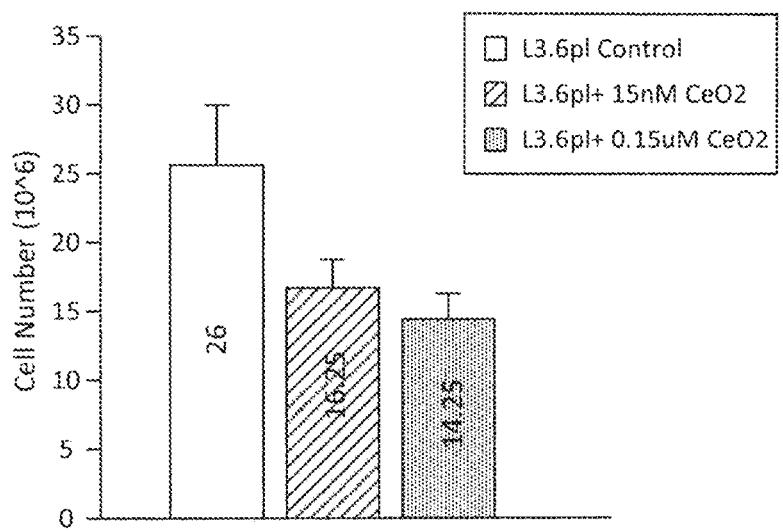
FIG. 7 is a graph of the results of a 48 h cell count study on L3.6p1 human pancreatic cancer cells.

FIG. 7 is a graph illustrating the results of a 48 h cell count study on L3.6p1 human pancreatic cancer cells, in order to determine the cytotoxicity of $CeO_2$. It was found that there was no significant difference in induction of cytotoxicity between 15 nM and 150 nM. The same results were obtained with an MCF-7 human breast cancer cell line.

Figure 8:
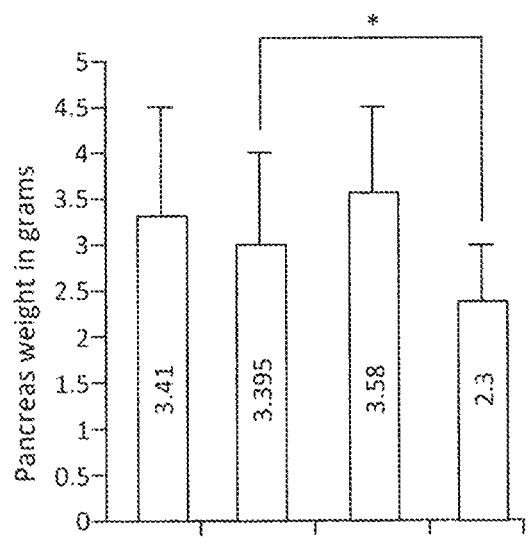
FIGS. 8,9 are graphs of the results of 6-week tumor weight (FIG. 8) and tumor volume (FIG. 9) studies on irradiated nude mice having human pancreatic cancer cells growing therein.

Another experiment studied the effects of $CeO_2$ nanoparticles on irradiated nude mice having had human pancreatic cancer cells injected therein. Mice were injected twice weekly intravenously with 100 uL of 15 nM (0,00001 mg/kg) $CeO_2$. and irradiated once a week with a fractionated does of 5 Gy for 6 weeks. FIG. 8 is a graph of the results of this experiment, showing that radiation alone does not reduce pancreatic tumor weight after the 6 weeks of radiation treatment (total of 35 Gy). In the presence of radiation, $CeO_2$-treated mice had a 37% decrease in tumor weight, as compared with radiation-treated mice.

Figure 9:
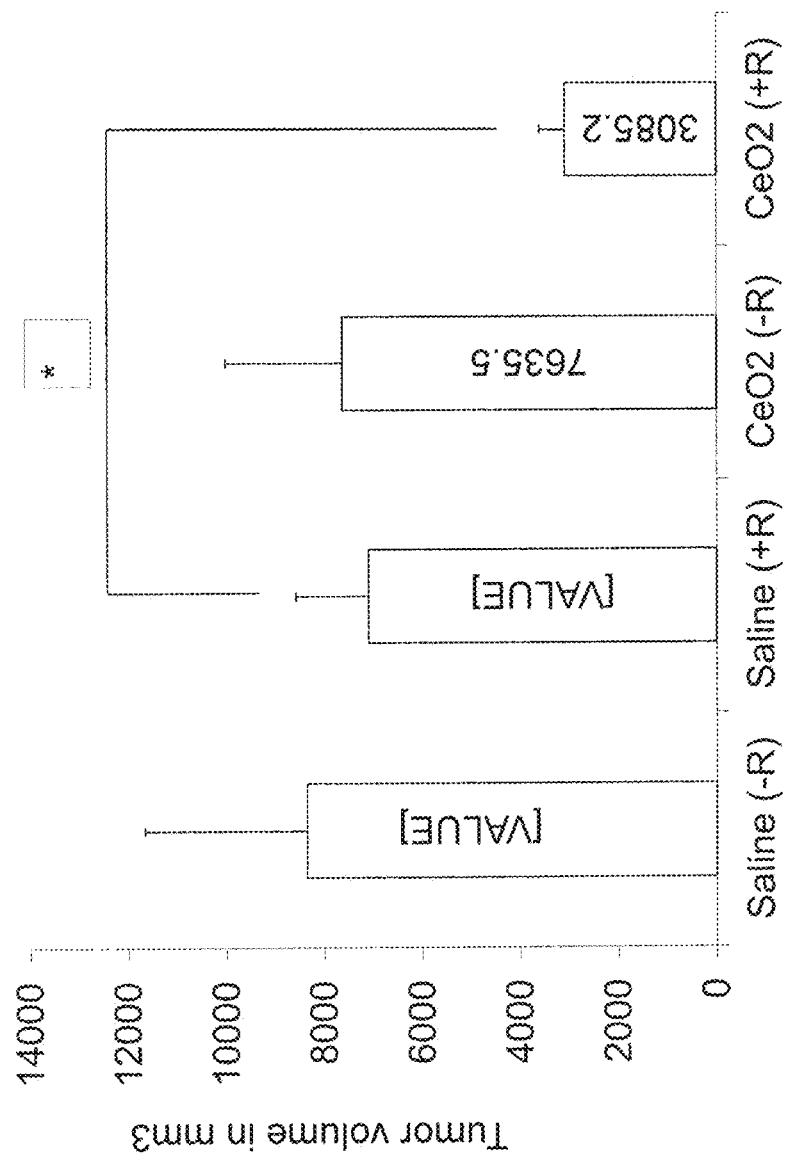

In a similar experiment (FIG. 9), the effects of $CeO_2$ nanoparticles on irradiated nude mice having had human pancreatic cancer cells injected therein were studied with regard to tumor volume. Again, mice were injected twice weekly intravenously with 100 uL of 15 nM (0.00001 mg/kg) $CeO_2$ and irradiated once a week with a fractionated dose of 5 Gy for 6 weeks. It was found that radiation alone reduced pancreatic tumor volume after the 6 weeks of radiation treatment (total of 35 Gy), and that $CeO_2$ as a single agent reduced pancreatic tumor volume. In the presence of radiation, $CeO_2$-treated mice had a 50% decrease in tumor volume as compared with radiation-treated mice.

Table 1 contains data on the results of treatment of orthotopically implanted pancreatic cancer cells by ionized radiation and cerium oxide nanoparticles.

TABLE 1

Treatment of Orthotopically Implanted L3.6p1 Human Pancreatic Cancer Cells by Ionized Radiation (R) and Cerium Oxide Nanoparticles (CeO$_2$)

| Treatment Group[1] | Tumor Incidence[2] | Tumor Volume (mm$^3$) | | Tumor Weight (g) | | Incidence of Liver Metastasis | Body Weight (g) | |
|---|---|---|---|---|---|---|---|---|
| | | Median | Range | Median | Range | | Median | Range |
| Saline Control | 10/10 | 7660.7 | 3435.5 to 11310.7 | 3.53 | 3.41-5.88 | 1/10 | 32 | 29-34 |
| Saline (R) | 10/10 | 6250.9 | 5645.4 to 8844.8 | 3.40 | 2.44-3.90 | 2/10 | 29 | 27-33 |
| CeO$_2$ (−R) | 10/10 | 6250.9 | 4485.8 to 9174.9 | 3.58 | 2.67-4.70 | 1/10 | 30 | 26-34 |
| CeO$_2$ (+R) | 10/10 | 3.043.8[3] | 3002.4 to 4206.3 | 2.3[4] | 1.30-2.78 | 1/10 | 27 | 24-32 |

[1] L3.6p1 human pancreatic cancer cells (1 × 10$^8$) were injected into the pancreas of nude mice. Ten days later, groups of mice were treated with vehicle solution, 5 Gy ionized radiation once weekly (30 Gy), twice weekly i.p. 15 nM cerium oxide NP, and a combination of 5 Gy ionized radiation once weekly (30 Gy), twice weekly i.p. 15 nM cerium oxide NP. All mice were killed on day 45.
[2] Number of positive mice/number of mice injected.
[3] $P < 0.005$ compared to control.
[4] $P < 0.01$ compared to control.

FIGS. 10A, 10B are reproductions of histological slides of pancreatic tumor tissue with radiation alone (FIG. 10A) and radiation plus cerium oxide (FIG. 10B). Here it is shown that CeO$_2$ nanoparticles sensitize tumor cells to radiation treatment and at the same time protect normal tissue. FIG. 10A shows an irradiated pancreatic tumor surrounded by non-functional pancreatic tissue. FIG. 10B shows an irradiated tumor surrounded by functional normal pancreatic tissue.

Figure 11:
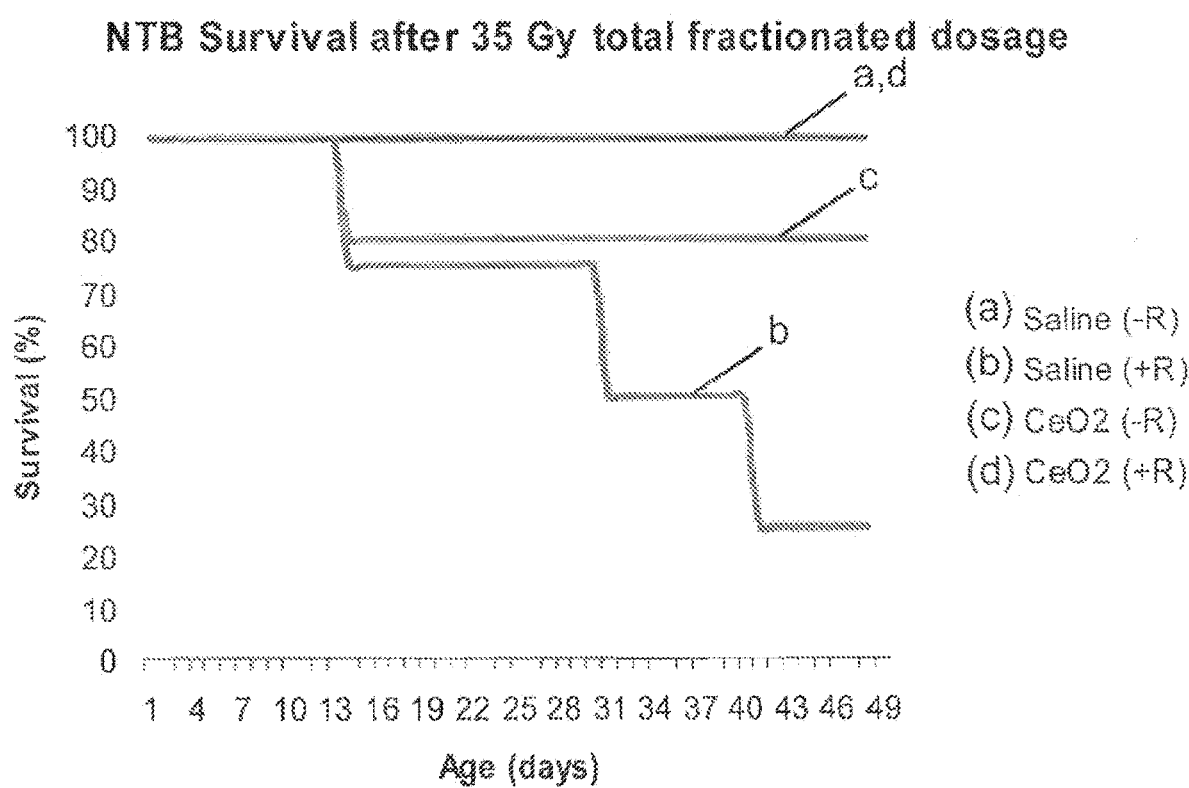
FIG. 11 is a graph of the effect of cerium oxide injections on the survival rate of non-tumor-bearing nude mice.

FIG. 11 is a graph of the effect of cerium oxide injections on the survival rate of non-tumor-bearing nude mice. As above, mice were injected twice weekly intravenously with 100 uL of 15 nM (0.00001 mg/kg) CeO$_2$, and irradiated once a week with a fractionated dose of 5 Gy for 7 weeks. Here it is shown that CeO$_2$ is well tolerated by the mice, and that no deleterious effects were observed in the CeO$_2$-treated group. Mice that received radiation alone (curve b) were found to succumb to radiation-induced death, but all the CeO$_2$-treated mice (curves c and d) survived the radiation treatment.

Figure 12:
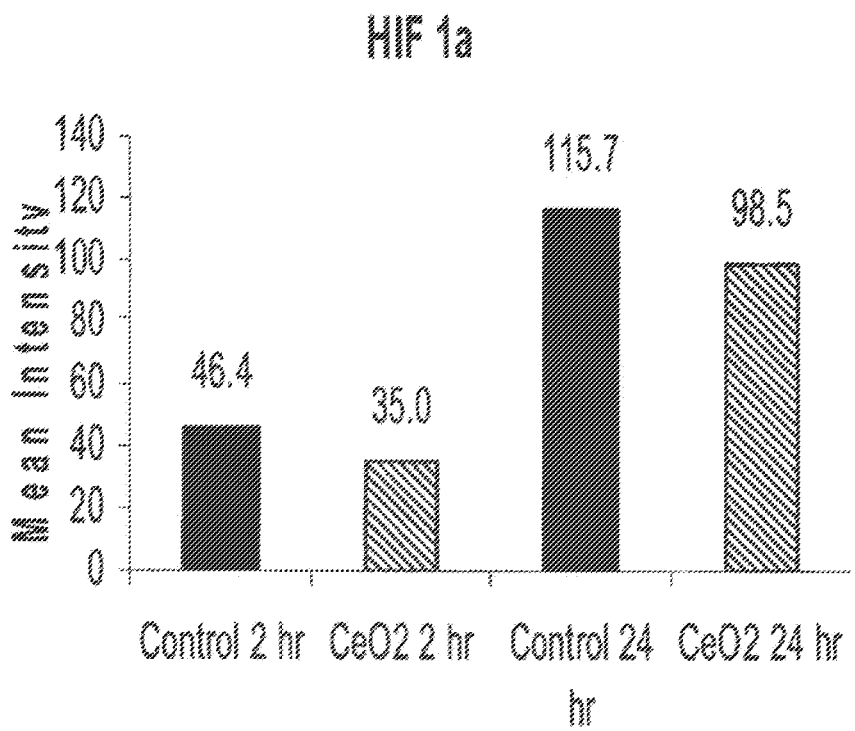
FIGS. 12,13 are graphs of the effect of hypoxia on L3.6p1 pancreatic cancer cells using HIF 1 a (FIG. 12) and HIF 2a (FIG. 13) as indicator, wherein FIG. 13 also includes a photograph of a gel from a Western blot assay of protein levels.
Figure 13:
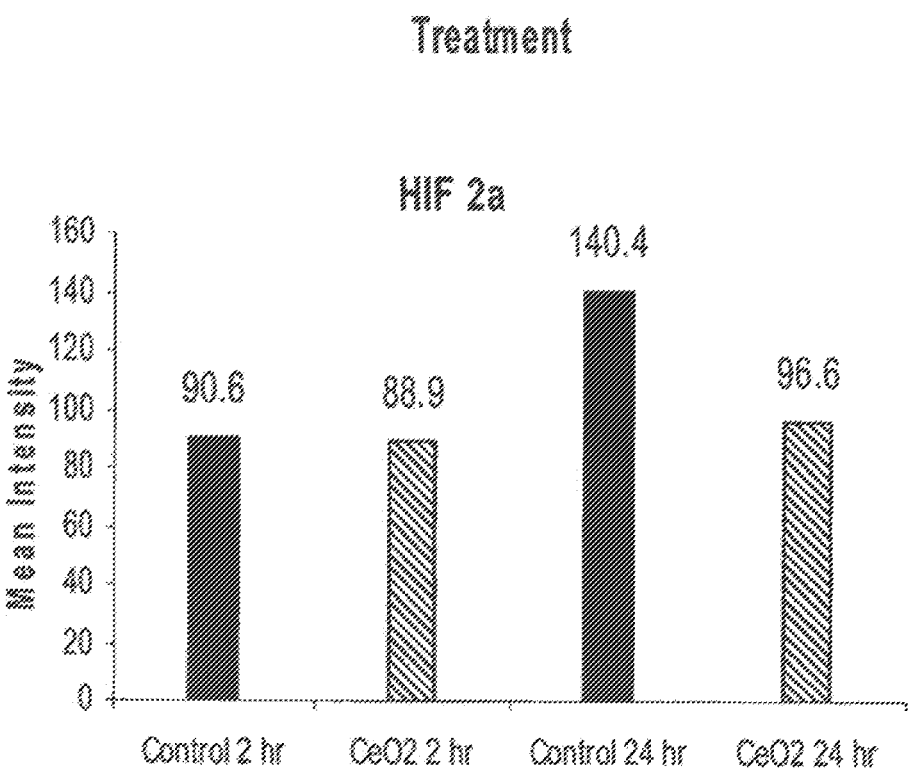

Hypoxia experiments were also undertaken, since it is known that CeO$_2$ acts as an oxygen buffer in low oxygen conditions. Tumors are hypoxic by nature; so the hypoxic microenvironment in the tumor makes the tumor resistant to radiation treatment, since oxygen is necessary for the production of superoxide radicals. For this study, L3.6p1 pancreatic cancer cells were exposed to a hypoxic environment for 5 h, and mRNA was extracted 2 and 24 h after induction of hypoxia. RT-PCT results for HIF 1a (FIG. 12) and HIF 2a (FIG. 13) demonstrated that cells treated with CeO$_2$ retained their baseline mRNA levels 24 h after hypoxia exposure. Beneath FIG. 13 are shown the results of a Western blot assay to prove that the same amount of protein was loaded onto the gel, and that, therefore, the changes in HIF that were measured reflect the effects of cerium oxide and not loading. It is hypothesized that CeO$_2$ oxygenates the tumor microenvironment, increasing tumor radiation sensitivity. HIF 1a and HIF 2a are overexpressed in cells under hypoxic conditions, and are transcription factors important in vascular development. Hypoxia is also known to contribute greatly to the pathophysiology of major categories of human disease, including myocardial and cerebral ischemia, cancer, pulmonary hypertension, congenital heart disease, and chronic obstructive pulmonary disease.

Figure 14:
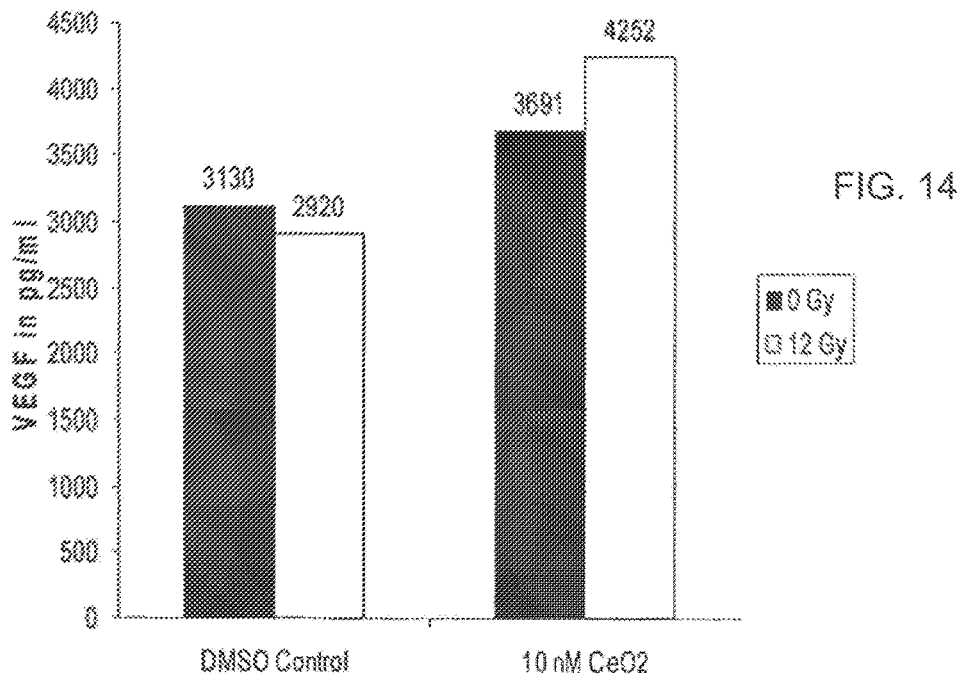
FIGS. 14,15 are graphs of the effects of cerium oxide on VEGF production by L3.6p1 human pancreatic cancer cells 24 h (FIG. 14) and 48 h (FIG. 15) after irradiation.
Figure 15:
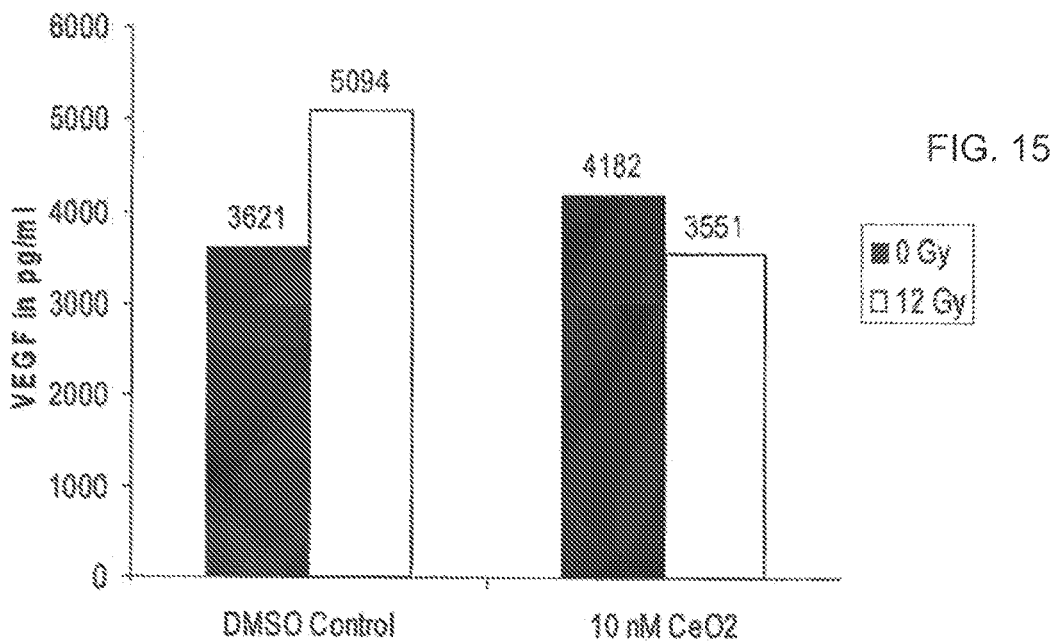

FIGS. 14 and 15 are graphs of the effects of cerium oxide on VEGF production by L3.6p1 human pancreatic cancer cells 24 h (FIG. 14) and 48 h (FIG. 15) after irradiation. In this study, VEGF concentration was determined from the cell culture supernatant, and it was found that CeO$_2$ slightly increased VEGF concentration on both non-irradiated (control) and irradiated cells. It was also found that 12 Gy irradiation increased VEGF production in the vehicle control, and that CeO$_2$ abrogated the VEGF production after radiation insult.

Figure 16:
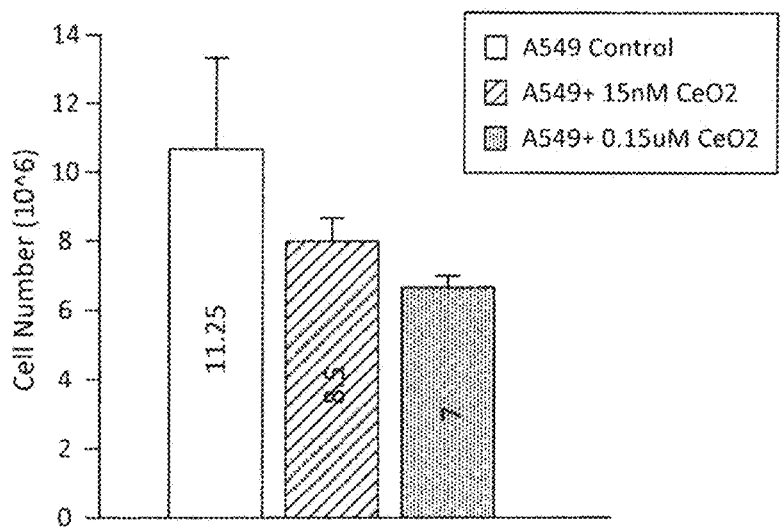
FIGS. 16,17 are graphs of the results of a 48 h cell count study on un-irradiated (FIG. 16) and irradiated (FIG. 17) A549 human lung cancer cells.
Figure 17:
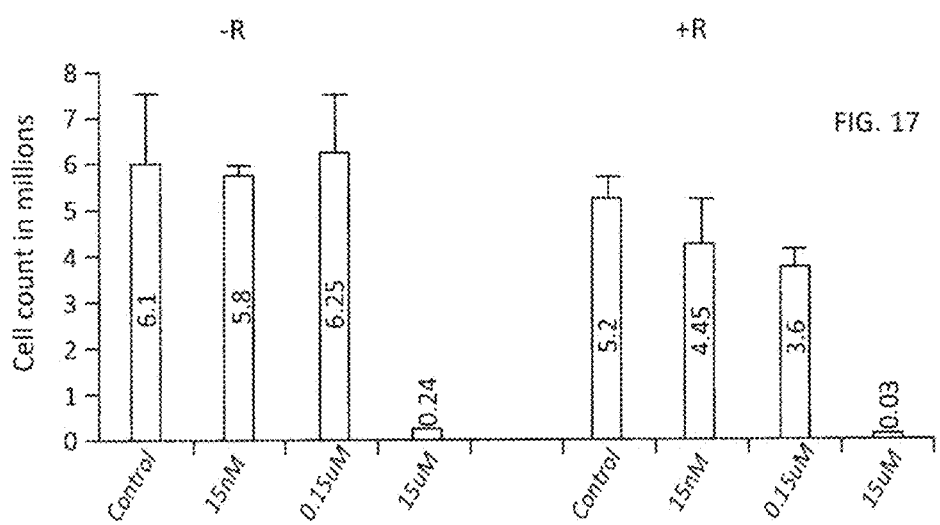
Figure 18:
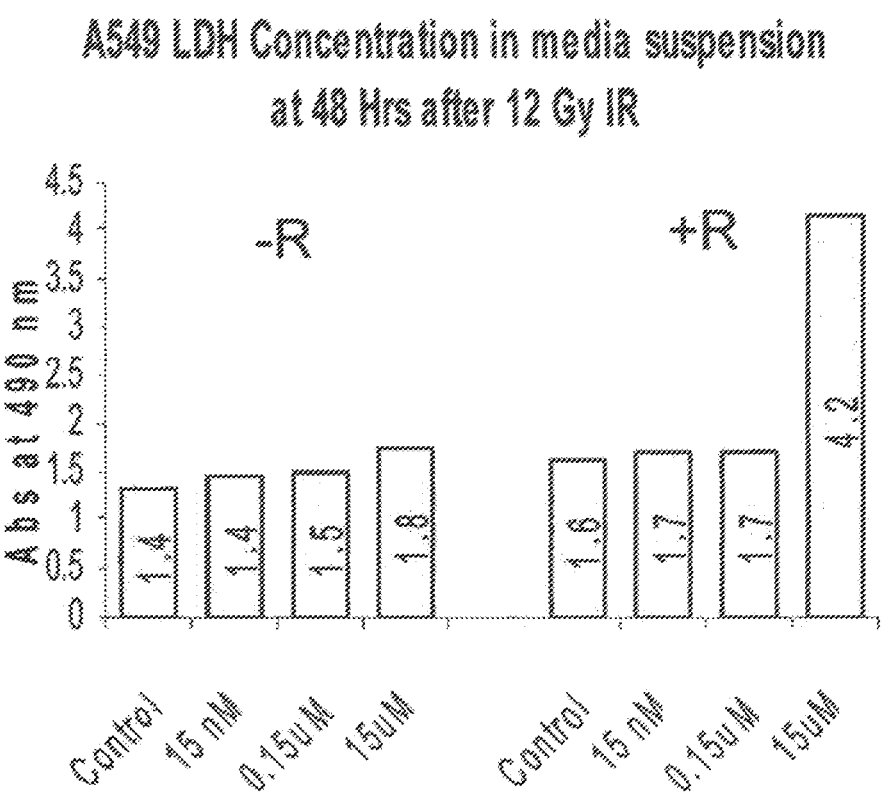
FIG. 18 is a graph of the results of a 48 h LDH study on irradiated A549 human lung cancer cells.

The effects of CeO$_2$ nanoparticles on A549 human lung cancer cells are illustrated in FIG. 16. A 48 h cell count assay was undertaken to determine cytotoxicity, with the result that, at high concentration CeO$_2$ is cytotoxic to this cell line in dose-dependent fashion. FIG. 17 also illustrates results of a 48 h cell count study on irradiated A549 human lung cancer cells. Here it is shown that, for these cells, the effect of CeO$_2$ is most significant at 15 µM, and that CeO$_2$ increases radiation-induced death in a dose-dependent manner. In addition, FIG. 18 further illustrates results of the effects of CeO$_2$ on irradiated A549 human lung cancer cells. A 48 h study included the testing of cell culture supernatant for the presence of LDH, which monitors for cell death. Again, as in FIG. 18, 15 µM CeO$_2$ was found to be the most significant concentration in the presence of radiation.

Figure 19:
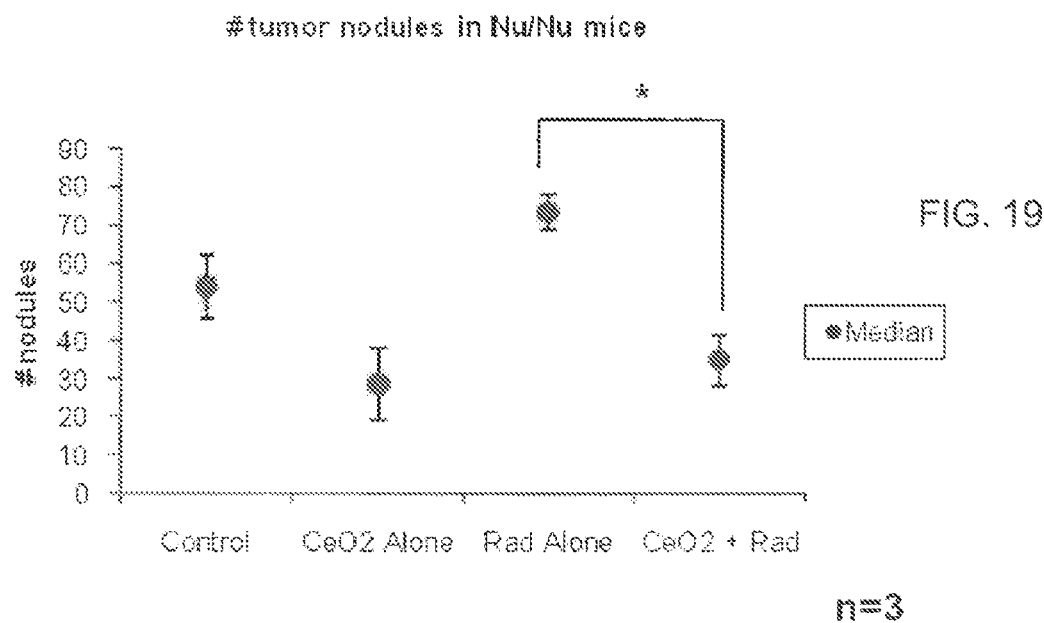
FIGS. 19,20 illustrate the results obtained on an orthotopic lung cancer model, wherein the number of tumor nodules in Nu/Nu mice (FIG. 19) and whole lung weight (FIG. 20) are plotted.
Figure 20:
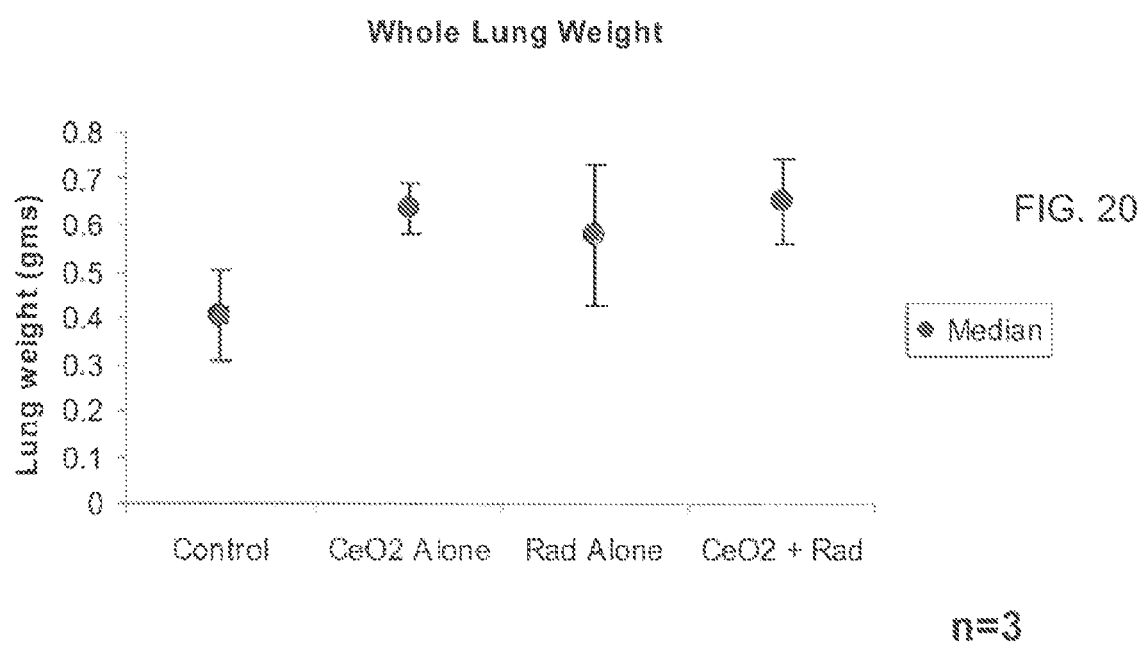

An orthotopic lung cancer model is illustrated in FIGS. 19 and 20, wherein the number of tumor nodules in Nu/Nu mice (FIG. 19) and whole lung weight (FIG. 20) are plotted for conditions with and without radiation, and with and without cerium oxide nanoparticles. It can be seen that the number of tumor nodules is significantly reduced in the presence of cerium oxide nanoparticles.

Another deleterious effect of radiation treatment for lung cancer is pneumonitis, the inflammation of lung tissue. Both in vitro (using normal lung fibroblast CCL 135 cells) and in vivo (using athymic nude mice lung tissue) experiments were performed to test the efficacy of CeO$_2$ nanoparticles in radioprotection of lung tissue.

Figure 21A:
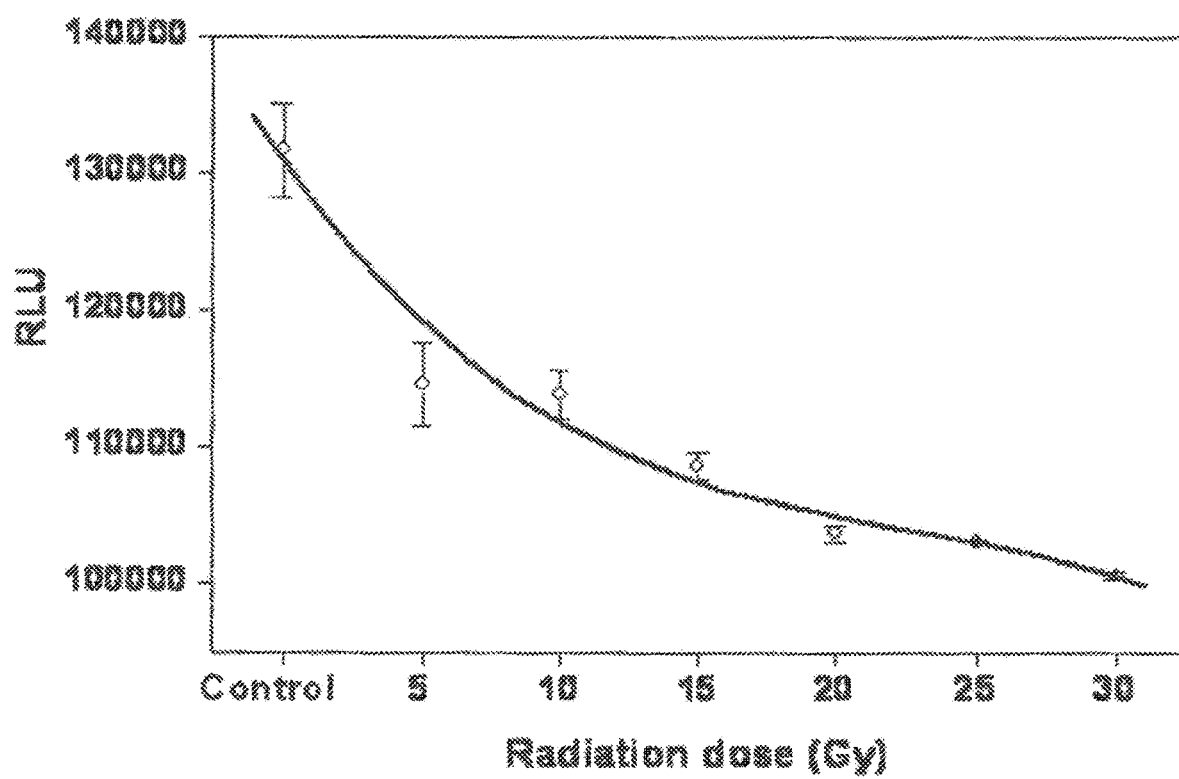
FIGS. 21A-21C illustrate the radioprotective effect of cerium oxide nanoparticles on normal lung fibroblasts, including a plot of cell viability versus radiation dose (FIG. 21A), cell viability under 20 Gy radiation with and without the presence of cerium oxide nanoparticles (FIG. 21B), and cell apoptosis under 20 Gy radiation, with and without the presence of cerium oxide nanoparticles (FIG. 21C)

For in vitro studies, the cells were trypsinized with a brief exposure to 0.25% trypsin and 0.02% EOTA, and 20,000 cells were delivered to 96-well plates in Oulbecco's Minimal Essential Medium (OMEM), supplemented with 10% fetal bovine serum. In the first set of studies, the cells were exposed to 0, 5, 10, 15, 20, 25, 30 Gy of radiation for 48 h. Radiation was performed on the 160-kV cell culture and small animal irradiator (radiation machine) from Kimtron Inc. (Woodbury, Conn.). Cell viability was determined by measuring the amount of ATP present, which signals the presence of metabolically active cells (FIG. 21A). The ATP is measured using the CellTiter-Glo luminescent Cell Viability Assay (Promega, Madison, Wis.). A direct relationship exists between luminescence measured with the CellTiter-Glo Assay and the number of cells in culture; therefore, the amount of ATP is directly proportional to the number of cells present. The detection of luminescence (RLU) is measured by a luminometer.

In the next set of experiments cells were treated with a predetermined optimal concentration of 10 nM of $CeO_2$ and exposed to a single dose of radiation (20 Gy).

Forty-eight hours later, cell viability (FIG. 21B) was determined by measuring the amount of ATP present, using the CellTiter-Glo Luminescent Cell Viability Assay (Promega, Madison, Wis.). In addition, the amount of caspase 3/7 activity (FIG. 21C) was measured by the Caspase-Glo 3/7 Assay (Promega, Madison, Wis.), and the amount of luminescence is proportional to the caspase 3/7 activity.

For the in vivo studies, athymic nude mice are housed in the specific pathogen-free (SPF) Cancer Research Institute animal facility which exceeds the national requirements for animal care, with two conventional mouse rooms, two nude mouse rooms, and one quarantine room. Radiation was administered using an IC160 X-ray cell culture and small animal irradiation system (Kimtron Inc., Woodbury, Conn., USA) located inside the animal facility. Nine weeks post radiation, the mice were sacrificed and the lungs were harvested and processed for hematoxylin and eosin (H&E) staining. For immunohistochemistry and hematoxylin and eosin-staining procedures, one part of the tumor tissue is formalin-fixed and paraffin-embedded and another part embedded in OCT compound (Miles, Inc., Elkhart, Ind.), rapidly frozen in liquid nitrogen, and stored at 200° C. for sectioning. Immunofluorescence microscopy is performed using a 20× objective on an epifluorescence microscope equipped with narrow bandpass excitation filters mounted in a filter wheel (Ludt Electronic Products, Hawthorne, N.Y.).

Figure 21B:
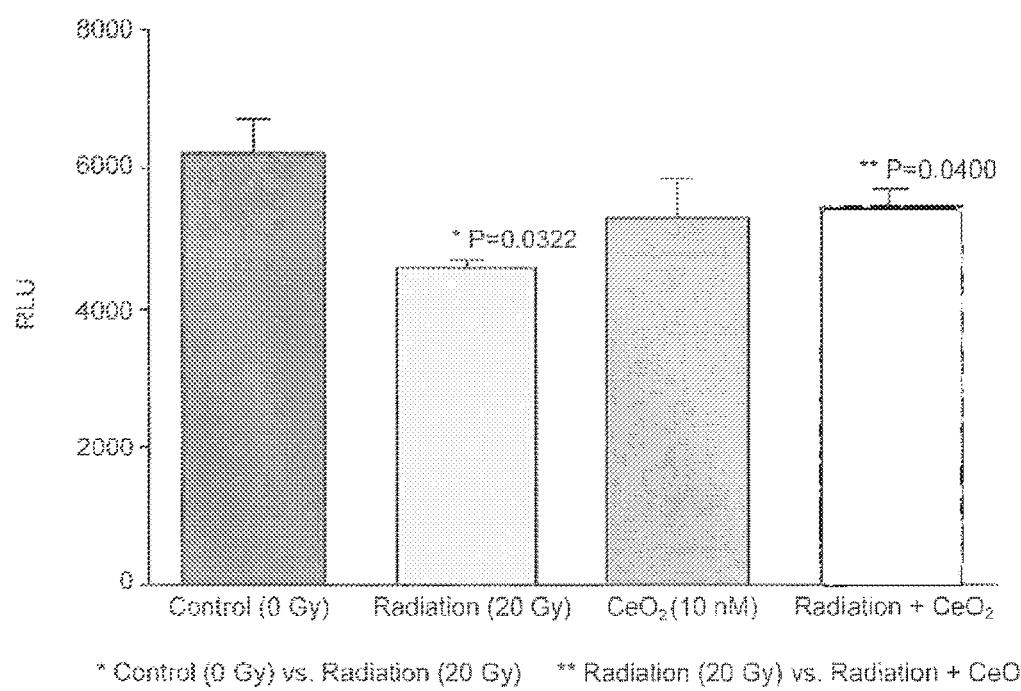
Figure 21C:
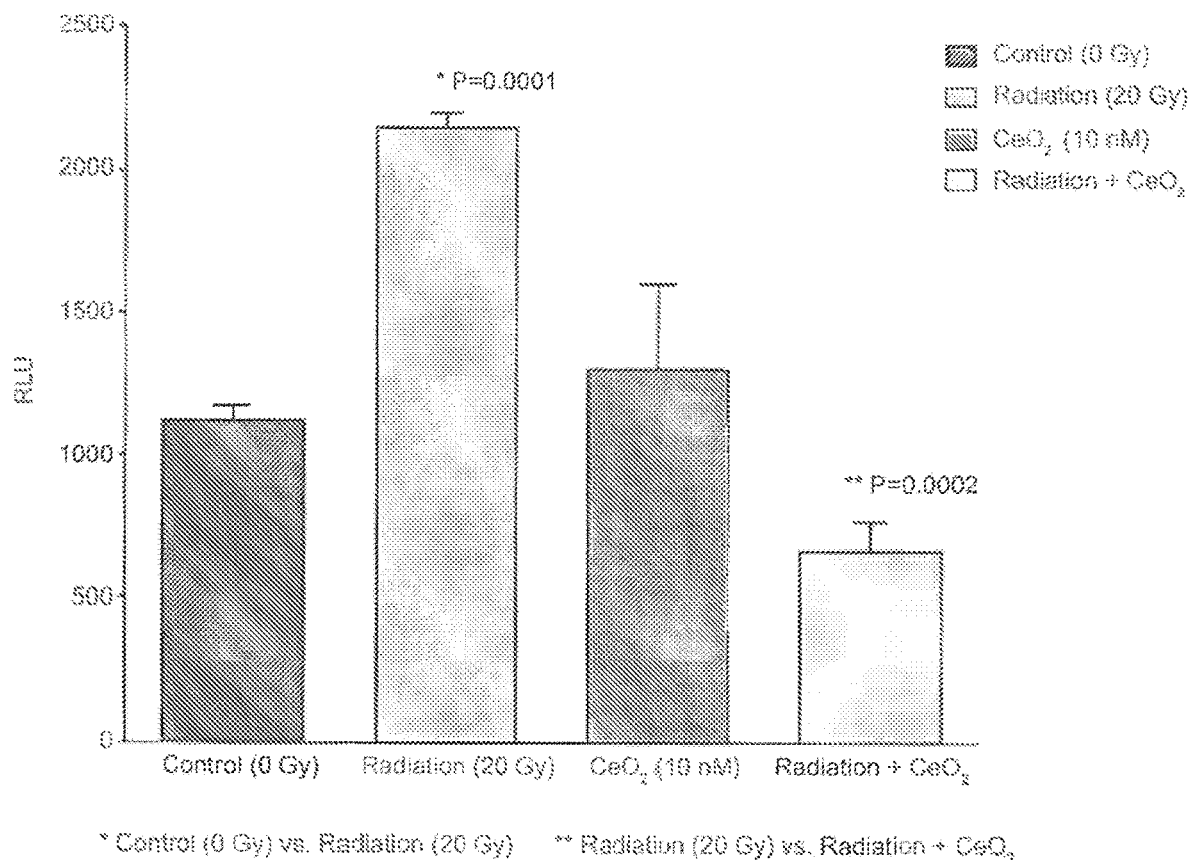

To obtain the results given in FIGS. 21A-21C, normal lung fibroblast (CCL 135) cells were exposed to increasing doses (5, 10, 15, 20, 25, 30 Gy) of radiation. The cell viability was measured by the quantification of ATP present, which signals the presence of metabolically active cells. As expected, results show a dose-dependent decrease in normal cell viability (FIG. 21A).

In the next set of experiments, the protective effect of $CeO_2$ nanoparticles on normal cells against radiation-induced cell damage was measured. Normal lung fibroblast CCL 135 cells were treated with a predetermined optimal concentration of 10 nM of $CeO_2$ and exposed to a single dose of radiation (20 Gy). Results show that when radiation was administered as single therapy, the number of viable cells in culture, as measured by Cell Titer-Glo luminescent Cell Viability Assay (which signals the presence of metabolically active cells), was significantly decreased. However, when $CeO_2$ was administered 24 h prior to radiation, the $CeO_2$ nanoparticles significantly protected the normal lung fibroblast cells from radiation-induced cell death (FIG. 21B).

In subsequent experiments, normal lung fibroblast CCI 135 cells were treated with a 10 nM concentration of $CeO_2$ and exposed to a single dose of radiation (20 Gy).

Forty-eight hours later, Caspase 3/7 activity (which signals the presence of apoptosis) was measured (FIG. 21C). When radiation (20 Gy) was administered as single therapy, the levels of Caspase 3/7 activity significantly increased as compared to control cells (no radiation). However, in the presence of $CeO_2$ the normal cells exposed to radiation were significantly protected and the activity of Caspase 3/7 was significantly decreased compared to control cells, and to cells exposed to $CeO_2$ alone, or radiation alone (FIG. 21C).

Figure 22A:
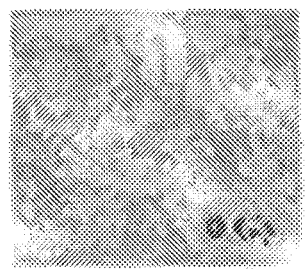
FIGS. 22A-22E illustrate radiation-induced pneumonitis and tolerance for cerium oxide nanoparticles in mice at different levels of radiation: 0 Gy (FIG. 22A), 12 Gy (FIG. 22B), 15 Gy (FIG. 22C), and 18 Gy (FIG. 22D), and survival under varying conditions with and without radiation, cerium oxide nanoparticles, and Amifostine (FIG. 22E)
Figure 22B:
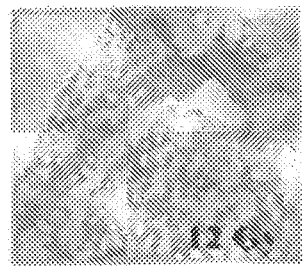
Figure 22C:
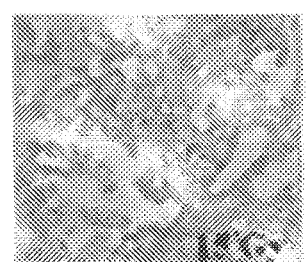
Figure 22D:
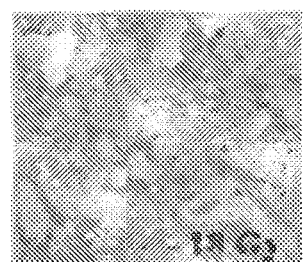

Radiation pneumonitis and subsequent pulmonary fibrosis can significantly decrease the quality of life of humans exposed to radiation. Therefore, in another set of experiments, a murine model of radiation-induced pneumonitis was established. A single dose of radiation (control, FIG. 22A; 12 Gy, FIG. 23B; 15 Gy, FIG. 22C; and 18 Gy, FIG. 220) was administered to the thoracic ventral area of non-tumor bearing athymic nude mice. Nine weeks post radiation, the mice were sacrificed, and the lungs were harvested and processed for hematoxylin and eosin (H&E) staining. Results indicate that a successful murine model of radiation-induced pneumonitis has been developed, and histology analyses show established pneumonitis in the lungs of those mice receiving 15 and 18 Gy of radiation (FIGS. 22C and 22D).

Figure 22E:
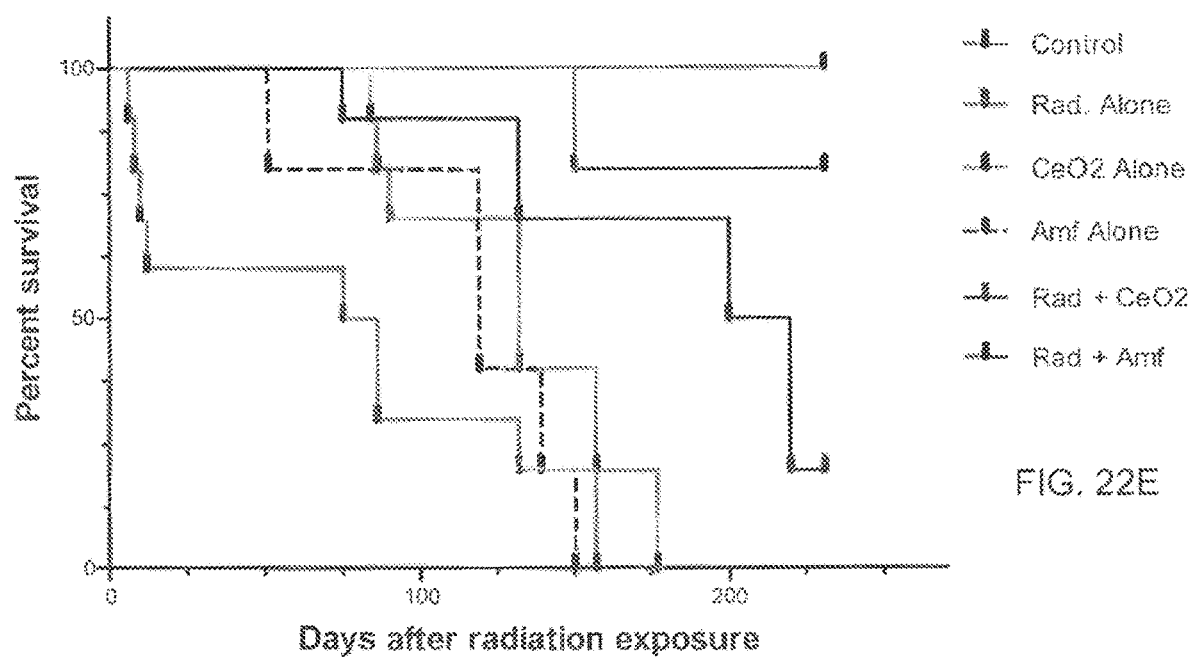

In an attempt to administer nanoparticles to live animals and to evaluate the radiation protection activity of $CeO_2$ the survival of non-tumor-bearing athymic nude mice was measured. Non-tumor-bearing athymic nude mice were exposed to fractionated doses of 30 Gy radiation (weekly administration of 5 Gy) in the presence or absence of twice weekly intravenous (i.v.) injections of $CeO_2$ or intraperitoneal (i.p.) injections of Amifostine 30 min prior to radiation. Nude mice (25 g) were randomized into the following groups: (1) weekly i.v. injections of saline (n=10, control group); (2) thrice weekly administrations of 5 Gy radiation (n=10); (3) twice weekly i.v. injections of 15 nM (0.00001 mg/kg) cerium oxide ($CeO_2$) nanoparticles (n=5); (4) thrice weekly i.p. injections of 150 mg/kg Amifostine (n=5); (5) administration of radiation combined with twice weekly i.v. injections of $CeO_2$ (n=10); and (6) administration of radiation combined with an Amifostine i.p. injection 30 min prior to radiation (n=10). Treatments continued for two weeks for a total dose of 30 Gy radiation. The mice were killed and necropsied only when they became moribund or the experiment was terminated. The weight and mortality of each mouse was measured throughout the experiment and median and percent survival was determined, as shown in FIG. 22E.

Results show that $CeO_2$ nanoparticles are well tolerated by athymic nude mice and protect mice from radiation-associated death. All control mice lived until termination date of 207 days. Interestingly, 80% of mice treated with $CeO_2$ alone were alive on termination date of 207 days. After treatment with radiation alone, Amifostine alone, and a combination of radiation and $CeO_2$. or radiation and Amifostine, the median survival time was 132, 119, 210, and 81 days, respectively (control versus radiation, $P<0.019$; control versus $CeO_2$, $P<0.66$; control versus Amifostine, $P<0.0370$; radiation versus radiation and $CeO_2$. $P<0.0041$; radiation versus radiation and Amifostine, $P<0.0432$). In contrast, Amifostine was highly toxic, as shown by the significant difference in median survival time (as compared with control mice). In summary, these results suggest that $CeO_2$ nanoparticles are well tolerated by mice and have a significant advantage over the clinically used Amifostine.

To determine the degree of radiation-induced pneumonitis, the lungs were harvested and processed for histology and H&E staining (FIGS. 23A-23D) and the amount of fibrosis and collagen deposition, indicative of chronic lung conditions, was measured using Masson's trichrome stain (FIGS. 23E-23H). The conditions include a control (FIGS. 23A, 23E), radiation alone (FIGS. 23B, 23F), radiation plus $CeO_2$ (FIGS. 23C, 23G), and radiation plus Amifostine (FIGS. 23D, 23H).

The lungs from mice in the control group (radiation alone, FIG. 23B) showed visible pneumonitis, with extensive macrophage invasion, whereas the lungs from irradiated mice receiving $CeO_2$ showed no visible pneumonitis and appeared normal (FIG. 23C).

In the experiments using Masson's Trichrome stain, the immunohistochemical analyses show that fibrosis and collagen deposition were common in the irradiated lungs of those mice given radiation alone (FIG. 23F) and of those mice given a pretreatment of Amifostine (FIG. 23H). Furthermore, immunohistochemical analysis indicated that collagen deposits were relatively recent, due to the faint blue stain, as compared to dark blue staining of older, more cross-linked collagen seen in human chronic lung diseases. In sharp contrast, no significant Trichrome staining was observed in normal lungs (control, FIG. 23E) or in those irradiated lungs of mice treated with $CeO_2$ (FIG. 23G).

Currently, there are very few reports regarding the biological effects of $CeO_2$ nanoparticles. Recent studies have shown that $CeO_2$ nanoparticles increase neuronal lifespan in culture. The biological activity of the $CeO_2$ nanoparticles was evaluated in a tissue culture model of rat cells and was shown to prolong brain cell longevity in culture by two- to three-fold. Furthermore, these nanoparticles reduced hydrogen peroxide ($H_2O_2$) and UV light-induced cell injury by over 60%. It has been proposed that $CeO_2$ nanoparticles act as regenerative free radical scavengers to give these beneficial effects in biological systems. The mechanism is based on the dynamic valence state of Ce ($Ce^{3+} \Longleftrightarrow Ce^{4+}$) in the $CeO_2$ nanocrystals.

The comparative Ce 3d x-ray photoelectron spectroscopy (XPS) spectra of micro and synthesized nano-cerium oxide particles are shown in FIG. 24, showing a high concentration of $Ce^{3+}$ in nanoceria compared with microceria particles. Peaks at 882.1 and 886 eV correspond to $Ce^{4+}$ and $Ce^{3+}$ peaks. Peaks at 918 eV correspond to satellite peaks indicating the presence of $Ce^{4+}$ peak. At nanoscale, the large surface area of cerium oxide leads to formation of more $Ce^{3+}$ due to ease of formation of oxygen vacancies. Such a high concentration of 0 vacancies and associated $Ce^{3+}$ cations gives high catalytic properties to cerium oxide nanoparticles. The free radical scavenging property of cerium oxide nanoparticles has been also attributed to the presence of oxygen vacancies. It is also suggested that there is an auto-regenerative reaction cycle continuing on the surface of cerium oxide nanoparticles, which provides an unprecedented antioxidant property.

The inset B of FIG. 24 is a high-resolution transmission electron microscopy (HRTEM) image of the synthesized nanoceria particles indicating the particle size of 3-5 nm with a fluorite lattice structure.

$CeO_2$ nanoparticles have been shown to confer protection against radiation-induced cell damage in normal lung fibroblast (CCL 135) cells and suggest that $CeO_2$ nanoparticles are an effective radioprotectant for normal tissues. Furthermore, $CeO_2$ nanoparticles appear to be well tolerated by treated animals, and seem to protect athymic nude mice against radiation-associated death, leading to a novel approach to radiation protection.

Another aspect of this radioprotection is the benefit to a patient who is scheduled for surgery following radiation treatment, since the irradiated normal tissue will tolerate the surgery better and heal more quickly from the surgery than radiation-damaged tissue.

It can be seen in the above results that $CeO_2$ is well tolerated by mice, and causes no toxicity to normal mice. $CeO_2$ also enhances radiation-induced cancer cell death, and protects normal tissue from radiation. Further, $CeO_2$ plus radiation controls/minimizes the metastatic index.

In an alternate embodiment of the above-disclosed invention, a topical cream composition for use in the radioprotection of skin is also provided. A plurality of compositions has been devised, each of which uses a "nanoactive solution," which is made as follows: A slurry is formed from a batch of 12% w/v ceria with 2% w/v Daxad, a sodium methacrylate acid-based surfactant. This slurry is stirred with the ingredients listed in Table 2 to form a smooth-spreading gel for spreading on the skin. In these compositions, Carbopol is a lightly cross-linked acrylic acid; Tween 80 is polysorbate 80, and the coconut oil is a fraction of whole oil in which the long-chain fatty acids are removed so that only the medium-chain saturated fatty acids remain. Centrifugation was performed for 15 min at 1380G.

TABLE 2

Sample compositions and characteristics

| Sample No. | Composition | Centrifugation Properties | pH | Rheometric Analysis Viscosity |
|---|---|---|---|---|
| 1 | 6.09 g of (10 mL 12% $CeO_2$ nanoactive soln + 0.2 g *aloe vera* powder + 0.2 g Carbopol 971) + 1 mL coconut oil + 200 μL Tween 80 | no settling | 4.75 | 2.70 ± 0.238 at 25° C.; 2.53 ± 0.232 at 37° C. |
| 2 | 4.4321 g essential wholesale shea butter cream + 1 mL 12% $CeO_2$ nanoactive soln + 200 μL PMB30W | very slight settling | 6.62 | 1.76 ± 0.093 at 25° C.; 0.409 ± 0.013 at 37° C. |
| 3 | 4.5278 g essential wholesale goat milk cream + 1 mL 12% $CeO_2$ nanoactive soln + 200 μL Tween 80 | no settling | 6.38 | 0.29 ± 0.004 at 25° C.; 0.073 ± 0.004 at 37° C. |
| 4 | 6.7908 (4.90 mL 12% $CeO_2$ nanoactive soln + 100 μL triethanolamine + 0.1 g *aloe vera* powder + 0.1 g Carbopol 971) + 1 mL coconut oil + 200 μL Tween 80 | no settling | 8.03 | 3.425 ± 0.107 at 25° C.; 2.468 ± 0.146 at 37° C. |
| 5 | 3 mL 12% $CeO_2$ nanoactive soln + 0.06 g *aloe vera* + 0.06 g Carbopol 971 + 556 μL coconut oil + 111 μL Tween 80 | | 4.71 | 3.873 at 25° C.; 2.918 at 37° C. |

TABLE 2-continued

Sample compositions and characteristics

| Sample No. | Composition | Centrifugation Properties | pH | Rheometric Analysis Viscosity |
|---|---|---|---|---|
| 6 | 6.5108 g (4.90 mL 12% CeO$_2$ nanoactive soln + 100 µL 1M NaOH + 0.1 g *aloe vera* powder + 0.1 g Carbopol 971) + 1 mL coconut oil + 200 µL Tween 80 | no settling observed, but slight water layer at top | 5.14 | 1.719 ± 0.078 at 25° C.; 1.376 ± 0.059 at 37° C. |
| 7 | 6.637 g (12% CeO$_2$ nanoactive soln + 100 µL triethanolamine + 0.1 g *aloe vera* powder + 0.125 g Carbopol 971) + 1 mL coconut oil + 200 µL Tween 80 | no settling | 7.77 | 4.131 ± 0.300 at 25° C.; 2.740 ± 0.176 at 37° C. |
| 8 | 5 mL 12% CeO$_2$ nanoactive soln + 0.1 g *aloe vera* powder + 2 mL coconut oil + 1 mL Tween 80 + 0.16 g Carbopol 971 | small white creamy layer had separated on top, but ceria did not settle out | 4.52 | 2.89 ± 0.031 at 25° C.; 2.497 ± 0.048 at 37° C. |
| 9 | 1.25 mL 12% CeO$_2$ nanoactive soln + 0.25 mL glycerin + 0.25 mL coconut oil + 0.5 mL safflower oil + 0.5 mL cocoa butter + 0.5 mL emulsifying wax | no phase separation upon centrifugation | 7.95 | 4.648 ± 0.112 at 25° C.; 1.932 ± 0.124 at 37° C. |

As of the filing of this application, the composition of Sample No. 9 has high viscosity and good "skin feel," as observed when spread evenly on human skin. This composition also has good stability and moderate pH. This composition is an emulsion of water and oil phase. The oil phase comprises safflower oil and fractionated coconut oil, both of which are in the liquid phase at room temperature along with cocoa butter and emulsifying wax, which are both solid at room temperature. The oil phase components were heated to liquefy. The water phase of ceria nanoactive solution and glycerin were also heated to 35° C. The oil phase was added to the water phase and mixed with a spatula. Agitation of the solution was continued for approximately 5 min to create an emulsion and ensure that the phase did not separate while cooling took place.

The role of nanoparticles as radioprotectants is a cutting-edge development regarding the protection of normal cells and tissues from radiation. The chemistry of engineered ceria nanoparticles supports a potential role as a biological free radical scavenger or antioxidant. Preliminary studies suggest that these nanoparticles may be a therapeutic regenerative material that will scavenge reactive oxygen species (ROS) that are responsible for radiation-induced cell damage. When biological systems are under high-energy exposure, such as in long-duration space exploration and extra-vehicular activity, astronauts are exposed to numerous sources of oxidative stress, including radiation, elevated oxygen exposure during extravehicular activity, and physical and psychological stress. When ROS are produced at high levels, cellular components can be damaged. These ROS can be used by biological systems as a defense mechanism against microorganisms and can act as signal transduction and transcription agents in development, stress responses, and programmed cell death. Oxidative stress arises from the strong cellular oxidizing potential of excess ROS, or free radicals. In addition, elevated levels of oxidative damage are related to increased risks for cataracts, cardiovascular disease, and cancer. Therefore, the potential benefit of the proposed radioprotection research is of great significance on multiple levels, one of which is its potential impact on human life. This invention is relevant to the health and quality of life of humans worldwide who are exposed to radiation environments, such as, but not intended to be limited to, astronauts in NASA exposed to particle radiation; military and civilians potentially exposed to radiation in battle, terrorism, or occupational exposure; and patients receiving radiation treatments for cancer.

Yet further, it was determined whether free radical scavenging cerium oxide nanoparticles (CONPs), at an optimal biological dose, sensitize pancreatic cancer cells to radiation. Radiation-induced $H^2O^2$ production was significantly increased in the presence of <10 µM of CONPs, whereas the production of $H^2O^2$ was significantly decreased in the presence of >20 µM CONPs. Radiation-induced ROS production was increased in L3.6p1 cancer cells pre-treated with CONPs, which correlated with a significant decrease in cell viability and clonogenicity as compared to radiation alone. Conversely, ROS was decreased in normal hTERT-HPNE cells without impacting cell viability. The volume of pancreatic tumors was reduced by 48% in mice treated with combination therapy compared to radiation alone. Immunohistochemical analysis showed that combination therapy resulted in a significant increase in tumor cell apoptosis. Collectively, our results show that CONPs sensitize cancer cells to radiation and may provide a novel radiation sensitizer for the treatment of human pancreatic cancer.

As illustrated with reference to FIGS. 25A(i-iv) and 25B (i-iv), CONPs selectively increase RT induced ROS in pancreatic cancer cells. With reference to FIG. 25A(i-iv), in L3.6p1 (FIG. 25(i, ii)) and hTERT-HPNE (FIG. 25A(iii, iv)) cells pre-incubated with CONPs, CONPs increased ROS production in pancreatic cancer cells (L3.6p1) lasting up to 24 hours, while transiently reducing ROS production in normal pancreatic cells (HPNE). As illustrated in FIG. 25B(i-iv), CONPs added after radiation did not impact ROS production inL3.6p1 cells (FIG. 25B(i,ii) but transiently decreased ROS production in HPNE cells (FIG. 25B(ii, iv).

FIGS. 26A-26D illustrate CONPs selectively sensitize pancreatic cancer cells to radiation in vitro. A. Pre-treatment of L3.6p1 cells with 10 µM CONPs increased radiation-induced decreases in cell viability by 1.7 fold. B. Pre-treatment of normal pancreatic cells (HPNE) with 10 µM CONPs had no significant impact on radiation-induced decreases in cell viability. C. Pre-treatment of L3.6p1 cells with 10 µM CONPs decreased radiation-induced colony formation by 2.4 fold. D. Results from FIG. 26C were quantified and graphed to illustrate the changes in colony formation.

Figure 27:
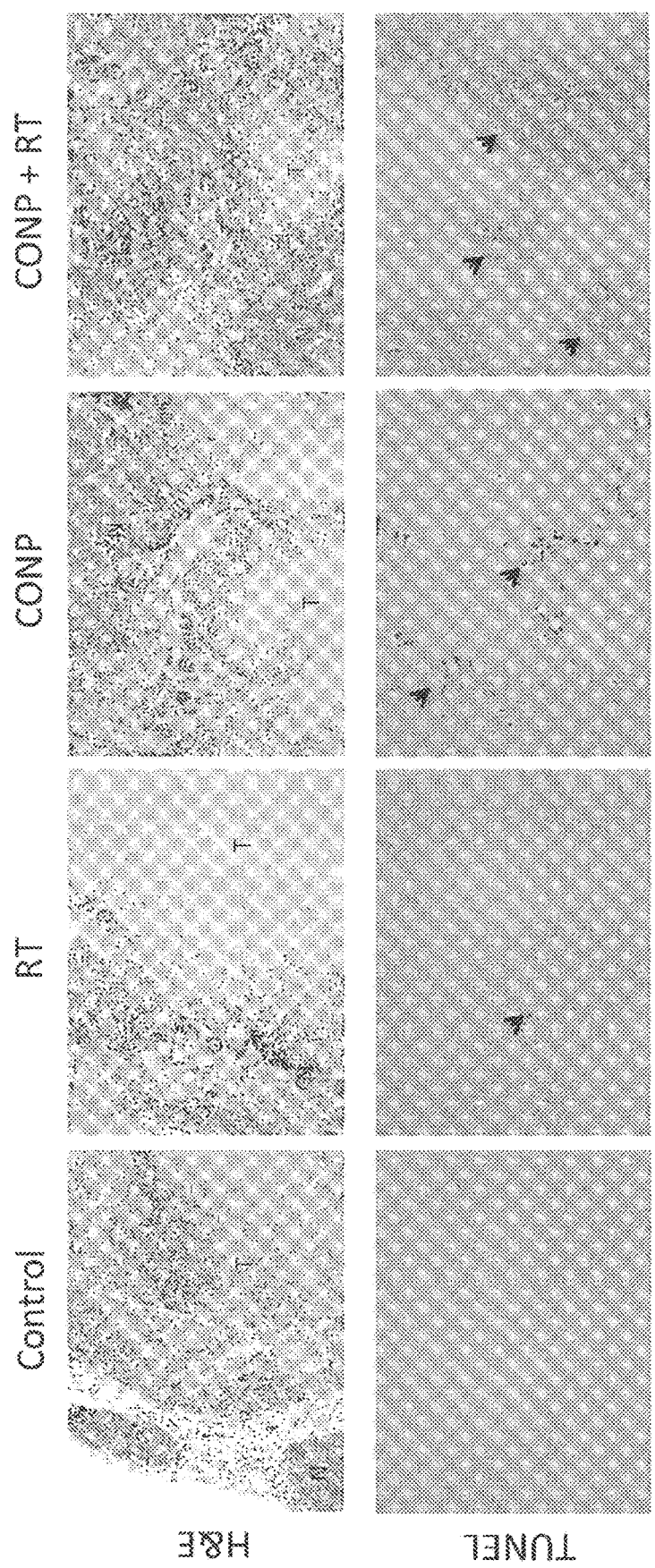
FIG. 27 illustrates CONPs drive radiation induced apoptosis in vivo.

FIG. 27 illustrates CONPs drive radiation induced apoptosis in vivo. H&E and TUNEL staining on tissue sections collected from mice showed CONP and, even more dramatically, combination (CONP and RT) treatment increased the amount of normal tissue present and the amount of radiation-induced apoptosis at the time of termination.

Detailed necropsy revealed that all of the mice had tumors in the pancreas. The data summarized in Table 3 show that the combination of CONP with radiation produced the greatest decrease in tumor weight as compared with radiation alone (0.97 g and 1.31 g, respectively; P<0.005). Body weight was not changed among all treatment groups as compared with control mice. No visible liver metastases were present (enumerated with the aid of a dissecting microscope) in any of the treatment groups.

TABLE 3

CONP increases pancreatic cancer cell sensitivity to radiation Pancreatic Tumors

| Treatment Group* | Tumor Incidence | Tumor Weight (g) | | Body Weight (g) | |
|---|---|---|---|---|---|
| | | Mean | Range | Mean | Range |
| Vehicle Control | 15/15 | 1.31 | 3.41-5.88 | 27.89 | 22.35-31.66 |
| CONP (15 µM) | 15/15 | 1.39 | 2.44-3.90 | 26.38 | 20.06-37-25 |
| Radiation (30 Gy) | 15/15 | 1.38 | 2.67-4.70 | 25.89 | 20.20-31.15 |
| CONP (15 µM) + Radiation (30 Gy) | 15/15 | 0.97* | 1.30-2.78 | 26.59 | 20.88-30.93 |

As above addressed, the teachings of the present invention address a novel approach for the protection of normal tissues against radiation-induced damage by using cerium oxide ($CeO_2$) nanoparticles. $CeO_2$ nanoparticles have been tested for their ability to serve as free radical scavengers to render protection against chemical, biological, and radiological insults that promote the production of free radicals. It was suggested that the unique structure of $CeO_2$ nanoparticles, with respect to valence and oxygen defects, promotes cell longevity and decreases toxic insults by virtue of its antioxidant properties, prevents the accumulation of reactive oxygen species (ROS), and thereby prevents the activation of the apoptotic response and cell death.

Previous work has tested the safety and ability of $CeO_2$ nanoparticles to confer radioprotection in a murine model. $CeO_2$ nanoparticles are well tolerated and appear to decrease the incidence of pneumonitis in athymic nude mice. In the instant disclosure, it is hypothesized that $CeO_2$ nanoparticles represent a novel approach to the protection of salivary and skin tissue from radiation-induced damage and test their efficacy as a new radioprotective compound on athymic nude mice receiving radiotherapy to the head and neck.

Figure 28A:
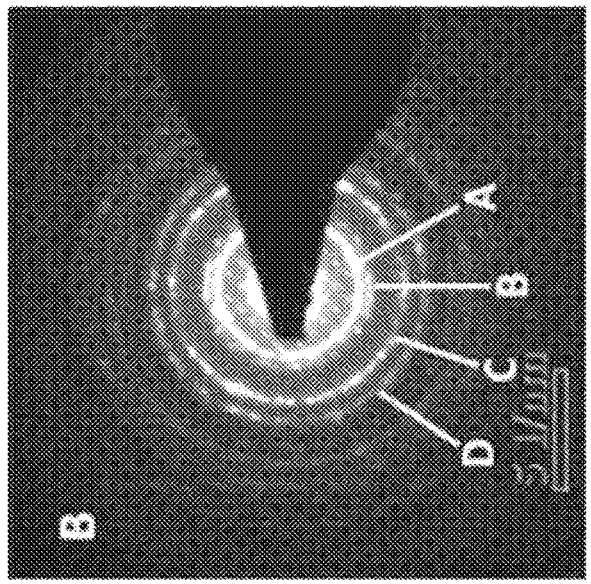
Figure 28B:
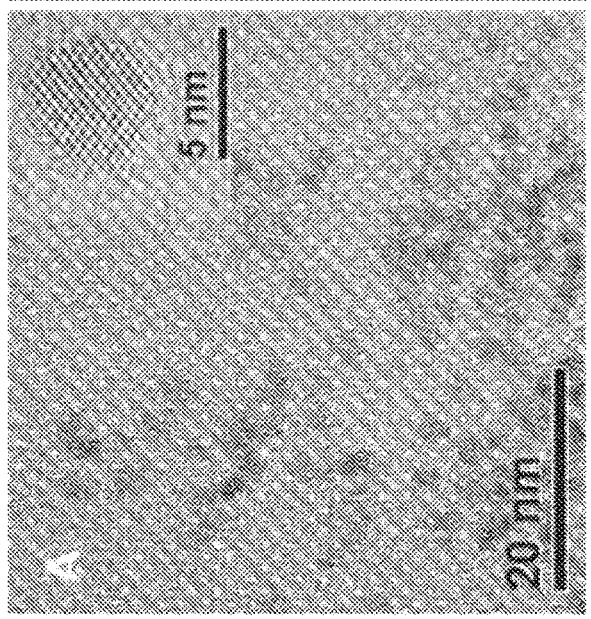
Figure 28C:
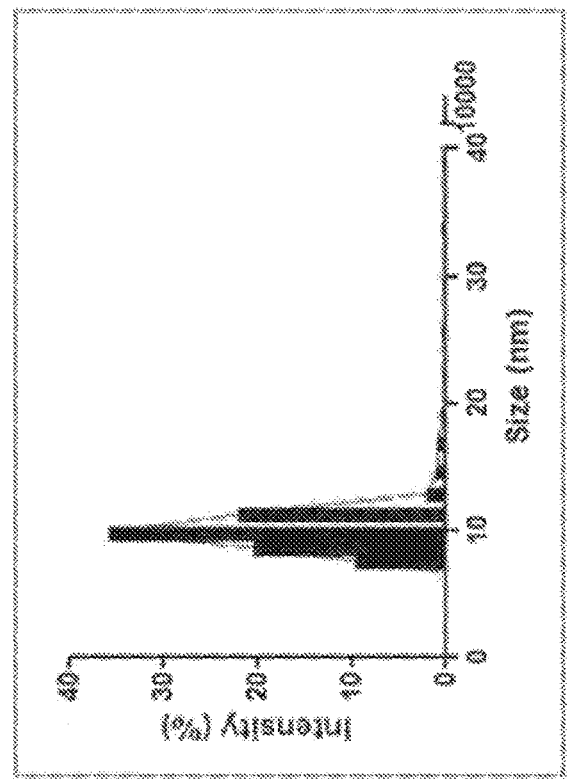

Tests were conducted and results found to support claims to that which is believed to be invention. By way of example, the flowing are herein reported:

$CeO_2$ Nanoparticles Synthesis and Characterization:

The cerium oxide nanoparticles were synthesized using a microemulsion process as previously described. Synthesized ceria oxide was examined by high-resolution transmission electron microscopy (HRTEM) to determine individual particle and agglomerate size. The physiochemical properties of the synthesized nanoparticles are illustrated in FIGS. 28A-28C. FIG. 28A illustrates HRTEM image of nanoceria showing nanoparticles size range of 3-5 nm, in the inset high magnification image of the nanoparticle. FIG. 28B illustrates a SEAD pattern of a the fluorite crystal structure where A, B, C and D corresponds to different lattice pattern 111, 200, 220 and 311, respectively, and FIG. 28C illustrates the hydrodynamic radius of the nanoparticle in the size range ~10 nm;

Animals: Female athymic nude mice (NCI-nu) were purchased from the Animal Production Area of the National Cancer Institute Frederick Cancer Research and Development Center (Frederick, Md.). Athymic nude mice were housed and maintained in the Cancer Research Institute's American Association for Accreditation of Laboratory Animal Care (AAALAC) accredited animal facility which exceeds the national requirements for animal care, with two conventional mouse rooms, two nude mouse rooms and one quarantine room. The use of animals for this study was and is approved by the MD Anderson Cancer Center Orlando Institutional Animal Care and Use Committee (IACUC) under the IACUC protocol number 09.06.01. Mice were used in accordance with institutional guidelines when they were 8-12 weeks of age.

Radiation and $CeO_2$ Nanoparticle Treatment of the Head and Neck Region of Athymic;

Nude Mice: The IC160 X-ray irradiation system (Kimtron Inc., Woodbury, Conn., USA) was employed to irradiate the head and neck region of the mice. The animals were anesthetized and placed in the supine position under the radiation focal spot. Irradiation was performed at room temperature with the use of a 160 kV X-ray generator unit operating at 18.5 mA at a rate of 2.74 Gy/sec. $CeO_2$ nanoparticles were delivered in 100 µL of saline by intraperitoneal (i.p.) injection as previously reported. A pilot study was performed in order to characterize the effects of radiation exposure to the head and neck area on salivary flow. The athymic mice were randomized into 5 groups (N=10/group). 1) no radiation (control group); 2) single radiation dose of 12.5 Gy; 3) single radiation dose of 15 Gy; 4) single radiation dose of 17.5 Gy; 5) single radiation dose of 20 Gy. Six weeks after the completion of radiation a sialometry analysis was performed.

In subsequent experiments, athymic nude mice cohorts underwent a two by three randomization. The mice were initially randomized into two cohorts (N=30/cohort): A) no radiation (mice were anesthetized and placed in the irradiator but did not receive radiation); B) 30 Gy of radiation fractionated in 6 doses (5 Gy/dose) given every other day over the course of two weeks. Then, each cohort was randomized into three groups (N=10/group): 1) bi-weekly intraperitoneal (i.p.) injections of saline for two weeks before radiation treatment and during the course of radiation treatment (control group); 2) bi-weekly i.p. injections of 15 nM (0.00001 mg/kg) $CeO_2$ nanoparticles for two weeks before the radiation treatment and during the course of radiation treatment; 3) biweekly i.p. injections of 15 µM (0.01 mg/kg) $CeO_2$ nanoparticles for two weeks before initiating radiation therapy and during the course of radiation therapy. A total of 8 injections of $CeO_2$ nanoparticles were given; four injections during the two weeks prior to radiation and four injections during the two week radiation course (i.e., two injections per week).

Radiation-Induced Damage—Evaluation Criteria:

Two independent double-blinded researchers graded radiation-induced dermatitis and hyperpigmentation at 1, 4, and 12 weeks after radiation therapy according to the National Cancer Institute (NCI) Common Toxicities Criteria's (CTC v. 3.0 Table 3.).

Anesthesia:

During evaluation of radiation dermatitis and saliva collection the mice were anesthetized with i.p. injections of Ketamine (100 mg/ml) and Xylazine (20 mg/ml) cocktail (1 µl/g of body weight).

Sialometry Analysis:

In the first set of experiments during which mice received escalating doses of single fraction radiation (12.5, 15, 17.5 and 20 Gy) without the administration of nanoparticles, mice were sacrificed at six weeks after the completion of radiation. In the next set of experiments, in which mice received 30 Gy of fractionated radiation (5 Gy/dose) with and without nanoparticles mice were terminated 90 days after the completion of radiation. Once anesthetized, the mice were weighed and salivary gland function was stimulated using subcutaneous injection of pilocarpine solution (50 mg/ml) at 2 mg/kg of body weight. Saliva collection began 10 minutes after the pilocarpine administration. Animals were placed in a vertex position facing up, and a pre-weighted 75-mm heparinized micro-hematocrit capillary tube (Drummond, Broomall, Pa.) was placed into the oral cavity. Whole saliva was collected for a 10 minute period and the amount of saliva collected was determined gravimetrically.

Necropsy Procedures and Histological Studies:

After the analyses of radiation-induced dermatitis and stimulated salivary flow were completed, all mice were sacrificed using a $CO_2$ chamber. The animals' body weight was recorded after sacrifice. All tissue necropsy, Hematoxylin and Eosin (H&E), and TUNEL analyses were performed on mice that received 30 Gy fractionated radiation (i.e., with and without 15 nM (0.00001 mg/kg) and 15 µM (0.01 mg/kg) $CeO_2$ nanoparticles). Harvested specimens from the oral cavity and neck included the tongue and adjacent soft tissues, parotid glands, sublingual glands, submandibular glands, and the regional lymph nodes. For H&E staining, these tissues were fixed in formalin, embedded in paraffin, and serially sectioned at 200 µM.

Paraffin-embedded tissues were used for TUNEL staining. TUNEL-positive cells were detected using the DeadEnd Colorimetric TUNEL System (Promega, Madison, Wis.)

Immunhistological microscopy was performed using a 40× objective on a Nikon E400 microscope (Nikon Instruments, Melville, N.Y.). Routine procedures were used to capture images, which were processed on Adobe Photoshop. Histological analysis was performed in collaboration with the pathology team of MD Anderson—Orlando. Immunopositive cells for TUNEL expression were counted per animal using a 40× objective over 10 individual slides and the average values were calculated.

Statistical Analysis:

Radiation-induced dermatitis and sialometry experiments were performed in triplicates and the data were presented as mean+SEM. Statistical analysis was done using Student's t test, assuming equal variance, and P value was calculated based on two-tailed test. A p value of <0.05 was considered statistically significant.

Results Included:

Validation of a Radiation-Induced Xerostomia Model:

Athymic nude mice were exposed to different doses of single fraction radiation (12.5 Gy, 15 Gy, 17.5 Gy or 20 Gy) and sialometry analysis was performed (FIGS. 29A-29C). Results indicate a dose dependent decrease in salivary function which is consistent with clinical observations reported on human patients undergoing radiotherapy to the head and neck.

FIGS. 29A-29C illustrate radiation effects on salivary production in the absence and presence of cerium oxide nanoparticles. (FIG. 29A) Stimulated sialometry analysis of salivary gland function 6 weeks after single fraction radiation to the head and neck area (12.5 Gy, 15 Gy, 17.5 Gy or 20 Gy). The results indicate a dose dependent decrease in salivary function with the greatest decrease in stimulated salivary flow after 15-17.5 Gy of single fraction radiation. (FIG. 29B) Effects of nanoceria ($CeO_2$) on salivary flow protection after radiation exposure. The results demonstrate a statistically significant difference in salivary flow production between the control group that received 30 Gy/6 fractions of radiation and mice treated with 30 Gy/6 fractions of radiation plus concomitant $CeO_2$ nanoparticles. (FIG. 29C) Effects of nanoceria ($CeO_2$) on skin hyperpigmentation after radiation exposure using the NC1 common terminology criteria for adverse events (CTCAE v.3.0). Mice treated with 15 nM (0.00001 mg/kg) $CeO_2$ nanoparticles demonstrated a lower incidence of grade II (33.33%) and a higher incidence of Grade I (66.67%) dermatitis. In contrast, mice treated with 15 µM (0.01 mg/kg) $CeO_2$ nanoparticles had an equal incidence of Grade I and II hyperpigmentation (50% each).

The greatest decrease in stimulated salivary flow was observed after 15-17.5 Gy of single fraction radiation. In order to simulate a more clinically relevant scenario, a fractionated schedule biologically equivalent to this single fraction regimen was devised. By a series of Biologically Effective Dose (BED) calculations [25], 30 Gy in 6 fractions of 5 Gy was used in subsequent experiments. This regimen has a BED of 45.0 Gy10 for acute effects and 80Gy3 for late effects, which compare favorably to the BED of a 15-17.5 Gy single fraction radiation regimen.

Furthermore, 30 Gy in 6 fractions would result in sufficient soft tissue effects and salivary gland dysfunction allowing adequate testing and evaluation of radioprotective properties of $CeO_2$ nanoparticles.

Effects of Cerium Oxide Nanoparticles on Salivary Function in the Absence of Radiation:

Sialometry analysis on non-radiated athymic nude mice previously exposed to i.p. injections of $CeO_2$ nanoparticles at 15 nM (0.00001 mg/kg) and at 15 µM (0.01 mg/kg) yielded no statistical difference in the mean salivary volume collected over 10 minutes, when compared to control no-nanoparticles (Saline) [Saline group vs. 15 nM (0.00001 mg/kg) group—p Value: 0.1007; Saline group vs. 1504 (0.01 mg/kg) group—p Value: 0.9856; 15 nM (0.00001 mg/kg) group vs. 1504 (0.01 mg/kg) group—p Value: 0.1159]. While the saline control group had a mean volume of 313 µL/10 min, the groups exposed to 15 nM (0.00001 mg/kg) and 15 µM (0.01 mg/kg) $CeO_2$ nanoparticles had mean volumes of 286 µL/10 min and 312 µL/10 min, respectively.

Effects of Cerium Oxide Nanoparticles on Athymic Nude Mice Exposed to Radiation to the Head and Neck Region:

The radiated groups that received either low concentration (15 nm; 0.00001 mg/kg) of $CeO_2$ nanoparticles or high concentration (15 µM; 0.01 mg/kg) of $CeO_2$ nanoparticles had an increase in salivary flow production when compared to the "no nanoparticle" radiated group 12 weeks after radiation exposure. Sialometry analysis demonstrated a statistically significant difference in salivary flow production between the control group that received 30 Gy/6 fractions of radiation and mice treated with 30 Gy/6 fractions of radiation that received concomitant treatment with $CeO_2$ nanoparticles. When the 15 nM (0.00001 mg/kg) and 15 µM (0.01 mg/kg) $CeO_2$ radiated groups were individually compared to the "no nanoparticle" radiated control group, there was a statistically significant difference in the stimulated salivary flow, favoring the 15 μM (0.01 mg/kg) CeO$_2$ group (P value: 0.0003, 95% CI: −128.0 to −52.90).

All of the skin hyperpigmentation observed in mice treated with radiation alone was recorded as Grade II. In comparison, mice treated with 15 nM CeO$_2$ nanoparticles demonstrated a lower incidence of grade II (33.33%) and a higher incidence of Grade I (66.67%) hyperpigmentation. Mice treated with 15 μM (0.01 mg/kg) CeO$_2$ nanoparticles had an equal incidence of Grade I and II hyperpigmentation (50% each).

Figure 30:
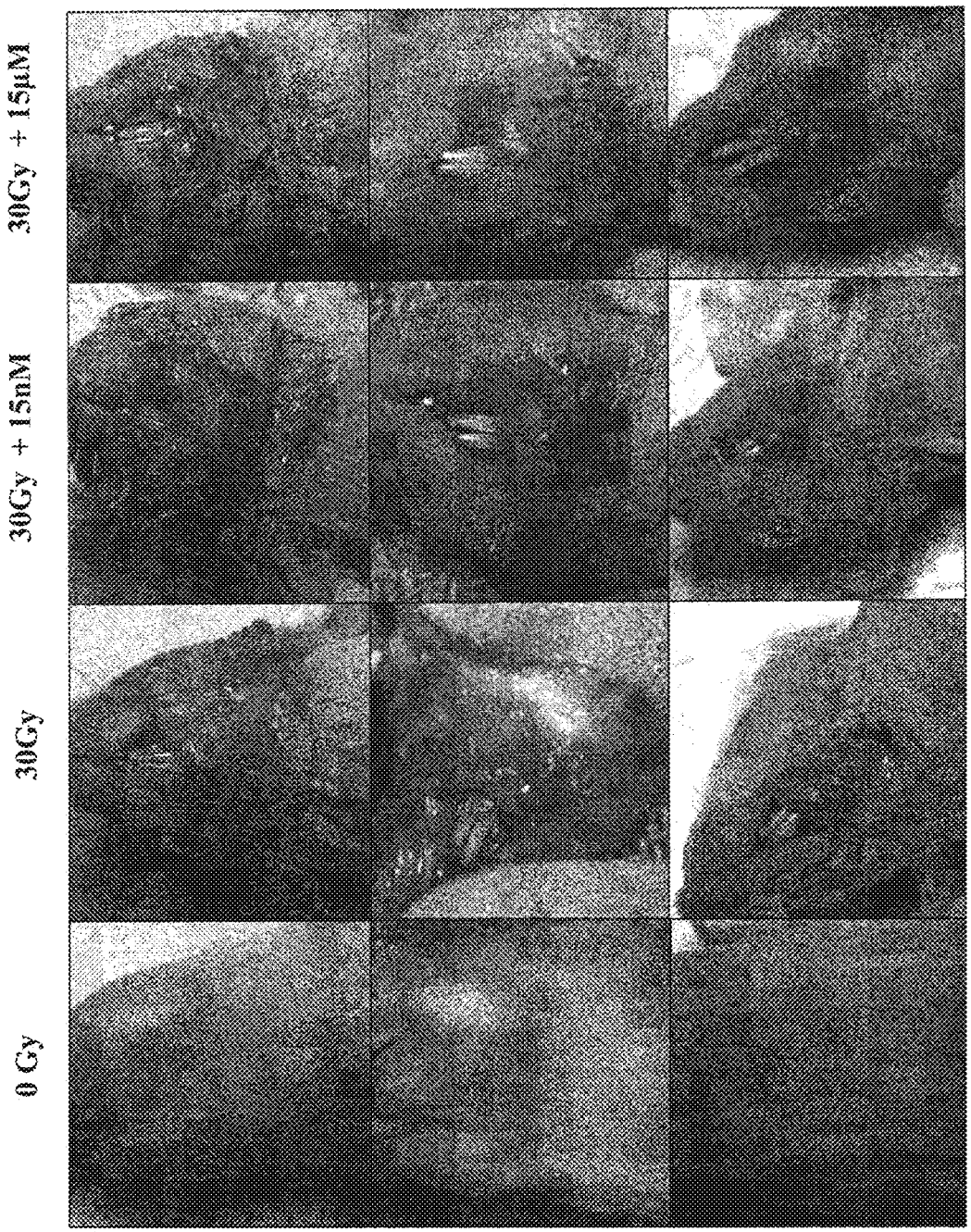
FIG. 30 illustrates macroscopic evaluation of radiation-induced dermatitis of athymic mice exposed to 30 gy in 6 fractions to the head and neck region.

An inverse correlation was observed between the incidence of Grade 3 radiation induced dermatitis and the concentration of CeO$_2$ nanoparticles given (FIG. 30). The incidence of Grade 3 dermatitis 1 week after radiation was decreased in the 15 μM (0.01 mg/kg) CeO$_2$ group compared to the non-CeO$_2$ controls (10% vs. 100% incidence of Grade 3 dermatitis, respectively). This effect was not appreciated in the 15 nM CeO$_2$ group. Furthermore, animals exposed to radiation and either 15 nM (0.00001 mg/kg) or 15 μM (0.01 mg/kg) concentration of CeO$_2$ nanoparticles showed swifter resolution of radiation dermatitis when compared to the control "no nanoparticle" radiated group. For example, complete healing was observed in 60% of animals pre-treated with 15 μM (0.01 mg/kg) of CeO$_2$ nanoparticles before radiation, vs 10% on the radiated control group, at 12 weeks postradiation (see FIG. 30).

Effects of Cerium Oxide Nanoparticles on the Apoptotic Index of Salivary Glands Parenchymal Cells After Radiation to the Head and Neck Region:

The parotid, sublingual and submandibular glands were independently analyzed and the acinar cell apoptotic index was determined using TUNEL analysis. Our results indicate a dose dependent decrease in the apoptotic index for the individual glands after radiation, indicative of the radioprotective nature of the nanoparticles (see FIGS. 31A and 31B).

Figure 31:
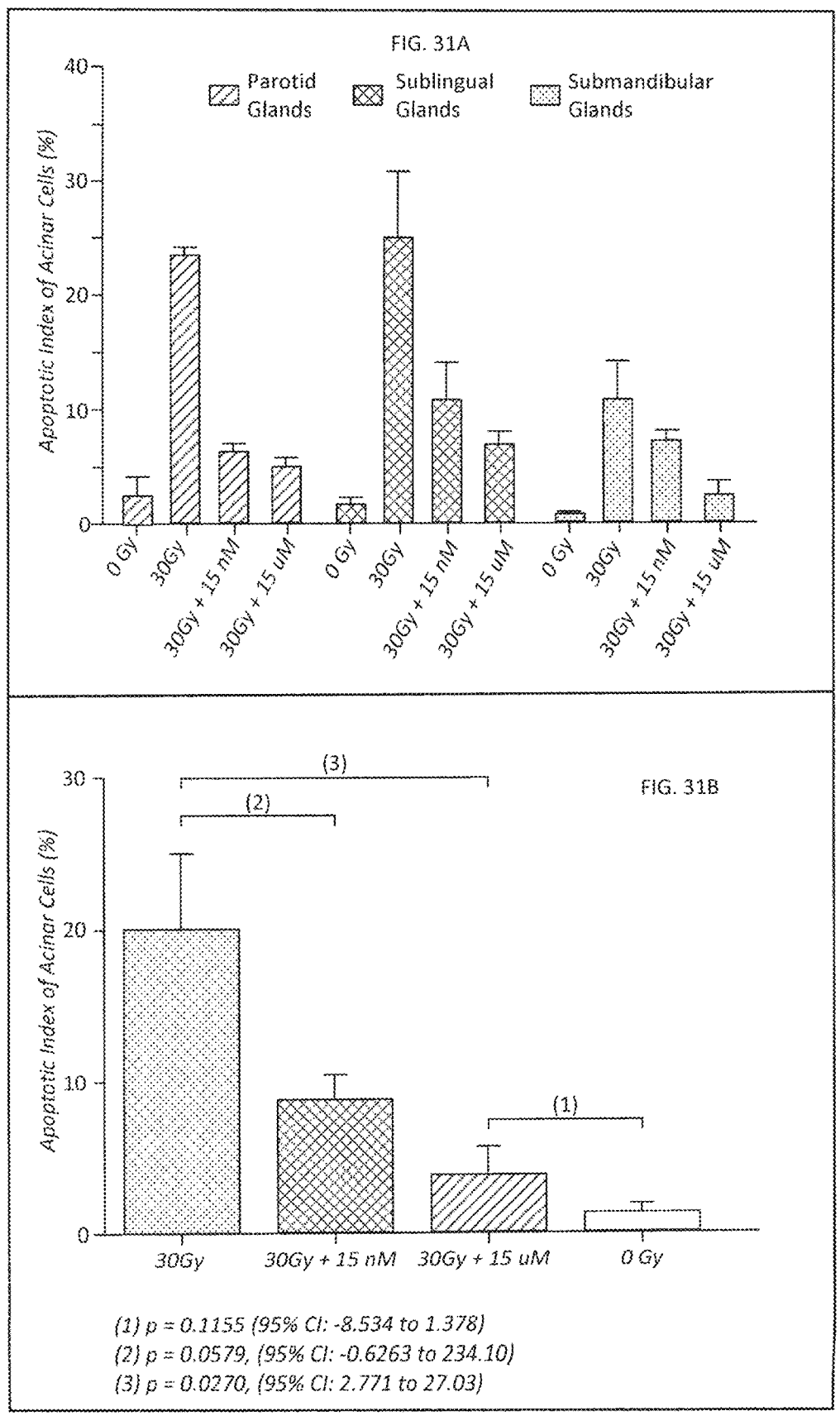

FIGS. 31A and 31B illustrate effects of cerium oxide nanoparticles on the apoptotic index of salivary glands parenchymal cells after radiation to the head and neck region. (FIG. 31A) Radiation-induced apoptosis of salivary glands (Parotid, Sublingual and Submandibular) parenchymal cells. The parotid glands of mice that given radiation, without CeO$_2$ treatment, showed an increase in apoptotic index (22%) compared to those that were not treated with radiation (2.2%) and to glands of mice that received either 15 nM (0.0000'1 mg/kg) or 15 μM (0.01 mg/kg) CeO$_2$ nanoparticles plus radiation (5.32% and 4.25%, respectively). Non-irradiated sublingual glands had a baseline apoptotic index of 1.87%, which increased to 26% after radiation. Pre-treating with either 15 nM (0.00001 mg/kg) or 15 μM (0.01 mg/kg) CeO$_2$ nanoparticles resulted in a reduction in the magnitude of apoptotic index elevation to 11.8% and 7.2%, respectively after radiation. Non-irradiated submandibular glands had a baseline apoptotic index of 0.2%. While radiation increased the index to 12.2%, by pre-treating with CeO$_2$ (15 nM (0.00001 mg/kg) or 15 μM (0.01 mg/kg)) the magnitude of elevation was decreased to 7.4% and 2.6% respectively. (FIG. 31B) Complementary analysis of the effects of CeO$_2$ nanoparticles combined with radiation on all major salivary gland yielded a similar response as that shown in FIG. 31A.

Complementary analysis of the effects of CeO$_2$ nanoparticles combined with radiation on all major salivary glands yielded a similar response. The overall apoptotic index baseline of acinar cells for the nonradiated group was 1.43%, while radiation-induced damage increased the apoptotic rate to 19.91%. Meanwhile, after treatment with radiation, both (15 nM and 15 μM; 0.00001 mg/kg and 0.01 mg/kg)) CeO$_2$ nanoparticle treated groups exhibited an apoptotic index of 8.17% and 4.67%, respectively. Statistical analysis demonstrated a significant difference between the "nonanoparticle" treated group and the 15 μM (0.01 mg/kg) CeO$_2$ treated group (p Value: 0.0270, 95% CI: 2.77 to 27.03). Lastly, a comparison between the group that received a combination of nanoparticles plus radiation and the control group (i.e. "no nanoparticle" "no radiation" controls) was performed to quantify the degree of radioprotection from apoptotic death compared to virgin salivary tissue. Comparison of the apoptotic index of the 15 μM (0.01 mg/kg) CeO$_2$ nanoparticle group that received radiation versus the "noradiation" "no-nanoparticle" control group showed no statistical difference (p Value: 0.1155, 95% CI: −8.534 to 1.378).

On the other hand, the apoptotic index of the 15 μM (0.01 mg/kg) CeO$_2$ nanoparticle treated group that did not receive radiation and the non-radiated "nonanoparticle" control group showed no statistical difference between them. These results suggest that exposure to CeO$_2$ nanoparticles does not result in adverse effects to acinar cells.

Figure 32:
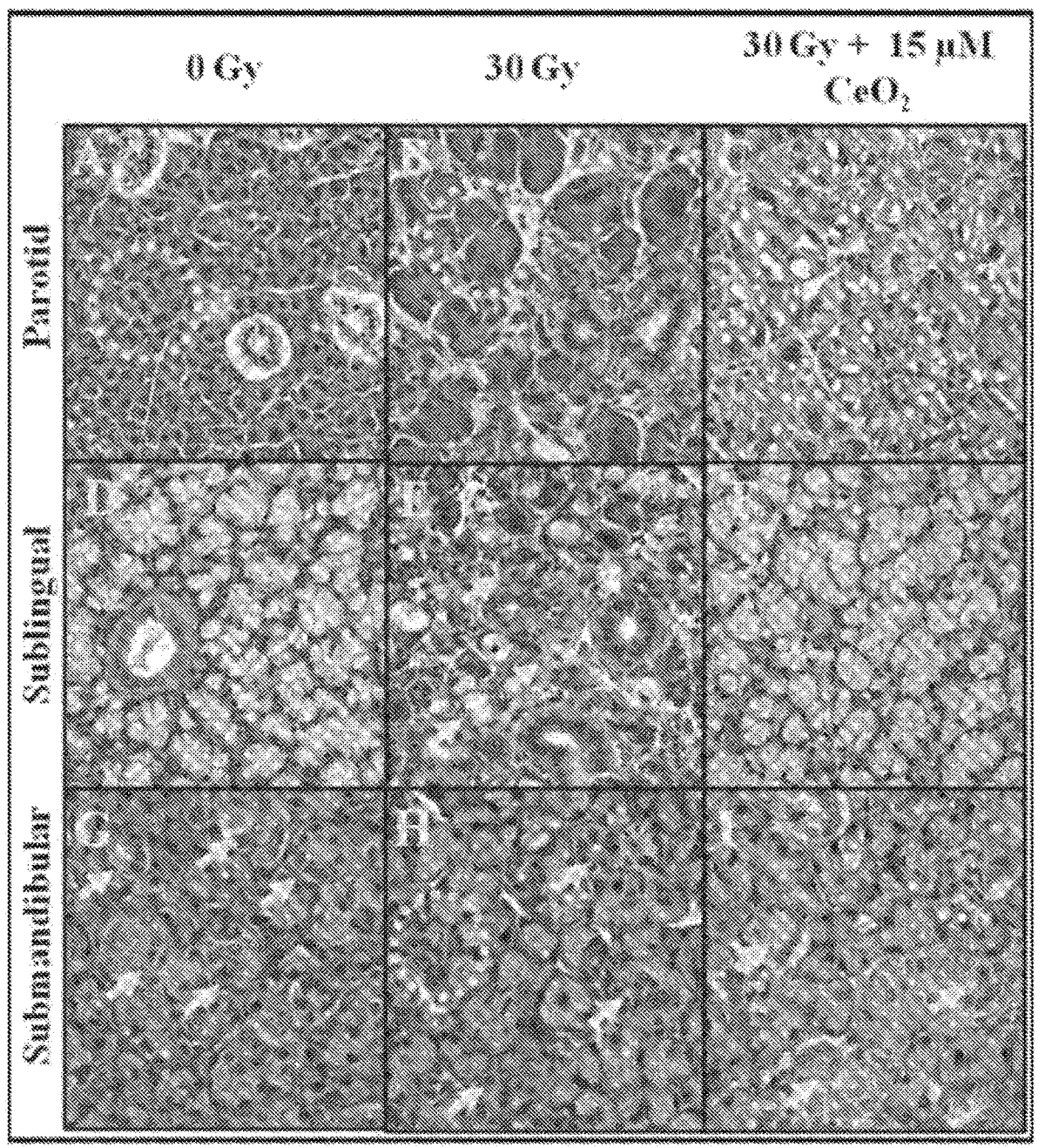
FIG. 32 illustrates a hematoxylin and eosin (H&E) analysis of radiation-induced damage on salivary glands parenchymal cell architecture.

H&E Evaluation of Radiation-Induced Damage on Salivary Gland Cell Architecture:

To determine the degree of radiation-induced damage to the salivary glands, the tongue, regional lymph nodes and soft tissue from the neck, these tissues were harvested and processed for H&E staining. The glands from mice in the irradiated control group (radiation alone) showed visible damage to their morphological architecture, with extensive macrophage and lymphocyte invasion. In contrast, the neck specimens from irradiated mice receiving either 15 nM (0.00001 mg/kg) (data not shown) or 15 μM (0.01 mg/kg) CeO$_2$ nanoparticles showed vacuolization of the acinar cells, but the overall morphology of the acinar tissue and number of acinar cell nuclei appears to be preserved (see FIG. 32).

F 1G. 32 illustrates H&E Analysis of Radiation-Induced Damage on Salivary Glands Parenchymal Cell Architecture. Shown are histologic evaluations using hematoxylin and eosin staining of harvested non-irradiated salivary gland specimens (A,D,G) [at 40× magnification]; gland specimens radiated with 30 Gy in 6 fractions (B,E, H) [at 40× magnification]; and specimens pretreated with 15 μM (0.01 mg/kg) of CeO$_2$ and subsequently irradiated (C,F,I) [at 40× magnification]. Morphologic analysis of parotid glands (Panel A: non-treated, non-irradiated group [yellow circle]) demonstrated preservation in the serous acinar architecture in the 15 μM (0.01 mg/kg) of CeO$_2$ irradiated group (Panel C, yellow circle) in contrast to radiation only specimens (Panel B, yellow circle) which shows destruction (yellow arrow) and hypertrophy of serous acinus. Sublingual gland analysis shows no alterations between the mucinous acinar structure of the non-treated, non-irradiated group and the 15 μM (0.01 mg/kg) of CeO$_2$ irradiated group (Panel D & F, yellow circle) when compared to the fibrotic changes, secondary to radiation, damage seen in the radiated only group (Panel E, yellow arrows). While the serous acinus architecture was preserved in the submandibular specimens there was a higher incidence of inflammatory cells (yellow circle) in the radiation only group. Meanwhile, the number of intralobular ducts was greatly decreased in the radiation only group (Panel H, yellow arrows) when compared to the non-treated, non-irradiated control group and the 15 μM (0.01 mg/kg) of CeO$_2$ irradiated group (Panel G & I, yellow arrows).

Radiation induced xerostomia, dermatitis, fibrosis, and mucositis are common and often severe complications of radiotherapy for head and neck cancer. One strategy to reduce normal tissue toxicity in this population of patients is the use of radiation protectors. The development of agents that can be employed to protect normal cells from the pernicious effects of radiation has been an active area of study since the 1950's. In an effort to combat these effects several free-radical scavengers have been tested. Presently, amifostine is the only agent in clinical use. Unfortunately, its short half-life, daily dosing requirements, and cost have been barriers to the widespread use of amifostine during radiotherapy for head and neck cancer. As a result, there remains a clinical need for a well-tolerated, facile, long-lasting, and cost-effective radioprotective agents; the "panacea" of radioprotection remains to be found.

Previous work has demonstrated the ability of $CeO_2$ nanoparticles to provide radioprotection to normal breast (CRL-8798) cells, but not to human breast cancer (MCF-7) cells at concentrations greater than 50 nM. Extension of this work demonstrated that $CeO_2$ nanoparticles protect gastrointestinal epithelium against radiation induced damage.

This work also suggests that $CeO_2$ nanoparticles confer radioprotection by acting as a free radical scavenger and by increasing the production of superoxide dismutase 2. Animal studies have demonstrated that $CeO_2$ nanoparticles are well tolerated in live animals. In addition, lung tissues harvested after whole-lung irradiation demonstrated no histological evidence of pneumonitis and fibrosis in athymic mice treated with 15 nM $CeO_2$ compared to "nonanoparticle" controls. In this current study, we are the first to show that $CeO_2$ nanoparticles may play a key role in the protection of tissues in the head and neck against radiation-induced damage that is possibly concentration dependent.

In this study, the assessment of stimulated sialometry strongly demonstrated improved salivary production in all $CeO_2$ nanoparticle treated groups compared to the "no-nanoparticle" radiated treated group. In the 15 μM (0.01 mg/kg) $CeO_2$ treated group the mean salivary flow after radiation was 65% of the non-radiated control, whereas in the 15 nM (0.00001 mg/kg) $CeO_2$ treated group the stimulated flow was approximately 50% of the non-radiated control. Therefore, $CeO_2$ appears to confer some degree of preservation of stimulated salivary function after radiation.

It is worth noting that salivary flow rates in the cohort of mice treated in the single fraction experiment (see FIG. 29A) were higher (even after 15-2OGy single fraction dose) than the flow rates in the fractionated experiment (see FIG. 29B). The argument could be made that hyposalivation is greater at three months compared to six weeks post-radiation. However, this is not what is suggested in the clinical literature. Clinical studies suggest that xerostomia is more intense immediately after radiation and begins to improve after a few months.

The explanation for this incongruence with clinical data on humans is unclear. The mice in the first experiment received single fraction radiation, which may be of different biologic significance than the fractionated course in the second experiment. Hence, it is difficult to compare sialometry results between the two groups.

There was a decreased incidence of radiation dermatitis in mice treated with 15 μM (0.01 mg/kg) $CeO_2$ nanoparticles that was not seen in the 15 nM (0.00001 mg/kg) $CeO_2$ nanoparticle group. However, the recovery from acute radiation dermatitis appeared to be more rapid in all groups that were pretreated with $CeO_2$ nanoparticles. TUNEL analysis demonstrated a decrease in cell death that was inversely proportional to the $CeO_2$ concentration. Lastly, it appears that salivary tissue architecture was preserved after radiation in mice receiving the highest concentration (15 μM; 0.01 mg/kg) of nanoparticles.

It is important to acknowledge that conflicting results have been published pertaining to the toxicity of $CeO_2$ nanoparticles [National Toxicology Program, National Institute of Environmental Health Sciences; National Institutes of Health; U. S. Department of Health and Human Sciences; Research Triangle Park, N.C. (www.ntp.niehs.nih.gov)]. However, these conflicting results can be resolved by accounting for variations in the nanoparticle's size, crystal structure and surface chemistry. Furthermore, the synthetic method, storage duration, and redispersion technique appear to play a major role in the biological application of $CeO_2$ nanoparticles. The culmination of these variations seems to determine the toxicity of $CeO_2$ nanoparticles. The $CeO_2$ nanoparticles used in this study were non-toxic in the concentrations evaluated. However, $CeO_2$ nanoparticles produced by different synthetic methods that are a different size and shape would be expected to have different toxicity. More experimentation is required to elucidate the specific role played by each of these characteristics.

The potential benefit of radioprotection conferred by the application of this technology could be significant. Most importantly, it could have a positive impact on patient's quality of life and improve the therapeutic ratio in the treatment of head and neck cancer. The application of agents such as $CeO_2$ alongside conformal techniques such as intensity modulated radiation (IMRT) and proton therapy, which allow tighter dose distributions around targets, may allow for more clear and categorical improvements in the quality of life of head and neck cancer patients. Moreover, this technology may have broad applications across the spectrum of human oncology treated with ionizing radiation.

The verification of the effectiveness of nanoparticles as radioprotectors opens the field for future studies that would examine, in depth, the mechanism, tissue distribution and safety of $CeO_2$ nanoparticles. Based on the findings of this study, our studies suggest the use of $CeO_2$ nanoparticles as a radioprotectant may be a feasible concept that should be tested in a larger cohort of athymic nude mice using a 15 μM (0.01 mg/kg) concentration of $CeO_2$. Moreover, it is important to note that any ambitious work in the field of radioprotection should use as a control the "gold standard", which after several decades of experimental and clinical evaluation, still remains amifostine. Clinical data suggests that amifostine does reduce the rate of acute and chronic xerostomia. Therefore, one of the future directions of this work is also to compare the tolerability and radioprotective ability of $CeO_2$ nanoparticles to amifostine.

In conclusion, this study suggests that $CeO_2$ nanoparticles may have a radiation protective effect on salivary production. Parallel observations indicate a reduction in Grade 3 radiation-induced dermatitis and skin hyperpigmentation. The use of $CeO_2$ nanoparticles as a radioprotectant may be a feasible concept, but the 15 μM (0.01 mg/kg) concentration should be tested in a larger cohort of animals. The long term objective of this work is to fully elucidate the safety, effectiveness, and tolerability of these agents in an orthotopic animal model.

In the foregoing description, certain terms have been used for brevity, clarity, and understanding, but no unnecessary limitations are to be implied therefrom beyond the requirements of the prior art, because such words are used for description purposes herein and are intended to be broadly construed.

In support of the above disclosure, reference is made to U.S. utility patent application Ser. No. 12/132,179 filed Jun. 3, 2008 for Cerium Oxide Nanoparticle Formulation for Use in Skin Cancer treatment and Tissue Radioprotection and Associated Methods, currently abandoned, the disclosure of which is herein incorporated by reference in its entirety. Reference is also made to Science Direct and Nanomedicine Journal research article titled: "Cerium Oxide Nanoparticles Protect Gastrointestinal Epithelium from Radiation-Induced Damage by Reduction of Reactive Oxygen Species and Upregulation of Superoxide Dismutase 2" January 2010, the disclosure of which is herein incorporated by reference in its entirety.

Although the invention has been described relative to various selected embodiments herein presented by way of example, there are numerous variations and modifications that will be readily apparent to those skilled in the art in light of the above teachings. It is therefore to be understood that, within the scope of the claims hereto attached and supported by this specification, the invention may be practiced other than as specifically described.

That which is claimed is:

1. A method of treating or protecting skin or salivary gland tissue from ionizing radiation induced dermatitis or reduced salivary production in a human in need thereof comprising topically applying an effective dose of a cerium oxide nanoparticle cream composition to skin of the individual; wherein the cerium oxide nanoparticle cream composition comprises 12% w/v cerium oxide nanoparticles; and wherein the cerium oxide nanoparticle cream composition demonstrates little to no settling upon centrifugation for 15 minutes at 1380G.

2. The method of claim 1, wherein the cerium oxide nanoparticles are non-agglomerated nanoparticles having a size in a range of 3 nm-5 nm.

3. The method of claim 1, wherein the effective dose of cerium oxide nanoparticles comprises a dose in a range of 10 nM-200 µM.

4. The method of claim 1, wherein the effective dose of cerium oxide nanoparticles comprises a dose of about 0.00001 mg/kg.

5. The method of claim 1, wherein the effective dose of cerium oxide nanoparticles comprises a dose of about 0.01 mg/kg.

6. The method of claim 5, wherein the microemulsion-derived cerium oxide nanoparticles have a size in a range of 3 nm-5 nm.

7. The method of claim 5, wherein the effective dose of cerium oxide nanoparticles comprises a dose in a range of 10 nM-200 µM.

8. The method of claim 5, wherein the effective dose of cerium oxide nanoparticles is administered before radiation exposure.

9. The method of claim 5, wherein the effective dose of cerium oxide nanoparticles is administered during radiation exposure.

10. The method of claim 5, wherein the effective dose of cerium oxide nanoparticles is administered after radiation exposure.

11. The method of claim 5, wherein the effective dose of cerium oxide nanoparticles is administered bi-weekly for about 2 weeks prior to radiation exposure.

12. The method of claim 5, wherein the effective dose of cerium oxide nanoparticles is administered bi-weekly for about 2 weeks during radiation exposure.

13. The method of claim 5, wherein the effective dose of cerium oxide nanoparticles is administered bi-weekly for about 2 weeks after radiation exposure.

14. The method of claim 5, wherein the cerium oxide nanoparticle cream composition further comprises 2% w/v of a sodium methacrylate acid-based surfactant.

15. The method of claim 5, wherein the cerium oxide nanoparticle cream composition further comprises carbopol, polysorbate, coconut oil, aloe vera powder, shea butter cream, goat milk cream, triethanolamine, glycerin, cocoa butter, emulsifying wax, safflower oil, or combinations thereof.

16. The method of claim 8, wherein the effective dose of cerium oxide nanoparticles is administered bi-weekly for about 2 weeks prior to radiation exposure.

17. The method of claim 9, wherein the effective dose of cerium oxide nanoparticles is administered bi-weekly for about 2 weeks during radiation exposure.

18. The method of claim 10, wherein the effective dose of cerium oxide nanoparticles is administered bi-weekly for about 2 weeks after radiation exposure.

* * * * *

UNITED STATES PATENT AND TRADEMARK OFFICE
CERTIFICATE OF CORRECTION

| | |
|---|---|
| PATENT NO. | : 11,116,792 B1 |
| APPLICATION NO. | : 14/860044 |
| DATED | : September 14, 2021 |
| INVENTOR(S) | : Cheryl H. Baker, D. Wayne Jenkins and Sudipta Seal |

It is certified that error appears in the above-identified patent and that said Letters Patent is hereby corrected as shown below:

On the Title Page

Item (71) Applicant: BioCurity Holdings, Inc. should be BioCurity Pharmaceuticals Inc., Jupiter, FL (US) and University of Central Florida Research Foundation, Inc., Orlando, FL (US)

Signed and Sealed this
Twentieth Day of September, 2022

Katherine Kelly Vidal
*Director of the United States Patent and Trademark Office*